United States Patent
Kobayakawa et al.

(10) Patent No.: US 12,076,325 B2
(45) Date of Patent: Sep. 3, 2024

(54) PROPHYLACTIC OR THERAPEUTIC AGENT FOR HYPOXIC INJURY, ISCHAEMIA-REPERFUSION INJURY AND INFLAMMATION, CELL PROTECTION AGENT FOR TRANSPLANTATION, AND BIO-PRESERVATION AGENT

(71) Applicant: SCENT SCIENCE INTERNATIONAL INC., Ibaraki (JP)

(72) Inventors: Ko Kobayakawa, Osaka (JP); Reiko Kobayakawa, Osaka (JP)

(73) Assignee: SCENT SCIENCE INTERNATIONAL INC., Ibaraki (JP)

( * ) Notice: Subject to any disclaimer, the term of this patent is extended or adjusted under 35 U.S.C. 154(b) by 0 days.

(21) Appl. No.: 18/099,200

(22) Filed: Jan. 19, 2023

(65) Prior Publication Data

US 2023/0149417 A1 May 18, 2023

Related U.S. Application Data

(63) Continuation of application No. 16/981,029, filed as application No. PCT/JP2019/010791 on Mar. 15, 2019, now Pat. No. 11,590,141.

(30) Foreign Application Priority Data

Mar. 16, 2018 (JP) .................. 2018-049761

(51) Int. Cl.
| | | |
|---|---|---|
| A61K 31/54 | (2006.01) | |
| A01N 1/02 | (2006.01) | |
| A61K 9/00 | (2006.01) | |
| A61K 31/26 | (2006.01) | |
| A61K 31/426 | (2006.01) | |
| A61P 9/10 | (2006.01) | |

(52) U.S. Cl.
CPC ............ *A61K 31/54* (2013.01); *A01N 1/0226* (2013.01); *A61K 9/0043* (2013.01); *A61K 31/26* (2013.01); *A61K 31/426* (2013.01); *A61P 9/10* (2018.01)

(58) Field of Classification Search
CPC .................. A61P 9/10; A61K 31/54
See application file for complete search history.

(56) References Cited

U.S. PATENT DOCUMENTS

| | | |
|---|---|---|
| 5,650,420 A | 7/1997 | Hall et al. |
| 9,198,427 B2 | 12/2015 | Kobayakawa et al. |
| 9,918,472 B2 | 3/2018 | Kobayakawa et al. |

FOREIGN PATENT DOCUMENTS

| | | |
|---|---|---|
| JP | H10-510809 A | 10/1998 |
| JP | 5350496 B2 | 8/2013 |
| WO | 96/14842 A1 | 5/1996 |
| WO | 03/075922 A1 | 9/2003 |
| WO | 2005/023815 A2 | 3/2005 |
| WO | 2005/023815 A3 | 3/2005 |
| WO | 2008/070741 A1 | 6/2008 |
| WO | WO 2008/070741 * | 6/2008 |
| WO | 2017/177200 A1 | 10/2017 |

OTHER PUBLICATIONS

Takahashi et al. (J. Agric. Food. Chem. (2008) 56:10462-10467). (Year: 2008).*
International Search Report, issued in International application No. PCT/JP2019/010791, dated Jun. 18, 2019.
Written Opinion of the International Searching Authority, issued in International application No. PCT/JP2019/010791 dated Jun. 18, 2019.
Stanetty, Peter et al., "Halogenated 2'-Chlorobithlazoles via Pd-Catalyzed Cross-Coupling Reactions," *J. Org. Chem.*, 2006, vol. 71, pp. 3754-3761.
Guo, Lei et al., "Theoretical evaluation of the corrosion inhibition performance of 1,3-thiazole and its amino derivatives" *Arabian Journal of Chemistry*, 2017, vol. 10, pp. 121-130.
Ung, T. Alison et al., "Asymmetric Synthesis of (1R, 2S,3R)-2-Acetyl-5-(1,2,3,4-tetrahydroxybutyl)thiazole" *Tetrahedron*, 1996, vol. 52, No. 44, pp. 14069-14078.
Vitzthum, O.G. et al., "Oxazoles and Thiazoles in Coffee Aroma" *Journal of Food Science*, 1974, vol. 39, pp. 1210-1215.
Yenari, Midori, et al. "Neuroprotective mechanisms of hypothermia in brain ischaemia," *Nature Reviews Neuroscience*, vol. 13, Apr. 2012, pp. 267-278.

(Continued)

*Primary Examiner* — Marcos L Sznaidman
(74) *Attorney, Agent, or Firm* — Sughrue Mion, PLLC

(57) ABSTRACT

A prophylactic or therapeutic agent for hypoxic injury, ischemia-reperfusion injury or inflammation, an agent for protecting cells for transplantation, and an agent for preserving organism are disclosed. A prophylactic or therapeutic agent for hypoxic injury, ischemia-reperfusion injury or inflammation, an agent for protecting cells for transplantation, or an agent for preserving organism, containing, as an active ingredient, at least one kind selected from a heterocyclic compound represented by the formula (I)

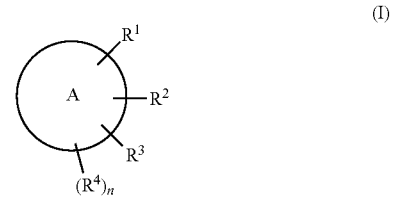

wherein each symbol is as described in the DESCRIPTION, or a salt thereof; an isothiocyanate compound represented by the formula $S=C=N-R^5$ (II) wherein the symbol is as described in the DESCRIPTION; and a TRPA1 agonist.

9 Claims, 19 Drawing Sheets

(56) References Cited

OTHER PUBLICATIONS

Hirai, Koichi et al., "A New Synthetic Method using Thiazoline Derivative" *Journal of Synthetic Organic Chemistry*, Japan, 1974, vol. 32, No. 1, pp. 20-32.

Pittet, Alan O. et al., "Comparative Study of Flavor Properties of Thiazole Derivatives" *J. Agric. Food Chem.*, 1974, vol. 22, No. 2, pp. 264-269.

Safar, Peter J., et al. "Therapeutic Hypothermia After Cardiac Arrest," *The New England Journal of Medicine*, vol. 346, No. 8, Feb. 21, 2002, pp. 612-613.

Kyros, L. et al., "Synthesis, characterization, and binding properties towards CT-DNA and lipoxygenase of mixed-ligand silver(1) complexes with 2-mercaptothiazole and its derivatives and triphenylphosphine" *J. Biol. Inorg. Chem.*, 2014, vol. 19, pp. 449-464.

Communication dated Nov. 18, 2021, issued in corresponding European Application No. 19766641.5.

Joichi, Atsushi et al., "Volatile constituents of blue-coloured hybrid tea rose flowers" *Flavour and Fragrance Journal*, 2013, vol. 28, pp. 180-187.

Kobayakawa, Ko, et al. "Innate versus learned odour processing in the mouse olfactory bulb" *Nature*, vol. 450: Nov. 22, 2007, pp. 503-508.

Laduranty, Joelle et al., "Chimie des radioprotecteurs: synthèese d'aikylamino-2 éthanethiols encombrés sur l'atome d'azote," *Can. J. Chem.*, 1987, vol. 65, pp. 859-867.

Olsen, Tom Skyhøj, et al. "Therapeutic hypothermia for acute stroke" *The Lancet Neurology*, vol. 2, Jul. 2003, pp. 410-416.

Testai et al., "The novel $H_2S$-donor 4-carboxyphenyl isothiocyanate promotes cardioprotective effects against ischemia/reperfusion injury through activation of mito$K_{ATP}$ channels and reduction of oxidative stress," *Pharmacological Research*, 2016, vol. 113, pp. 290-299.

Yavari, Issa et al., "A synthesis of functionalized arylthio-acrylates, benzo[b][1,4]thiazines and benzo[4,5]thiazolo[3,2-a]azepines from 2-methylbenzothiazole and acetylenic esters in aqueous media," *Mol. Divers.*, 2017, vol. 21, pp. 527-532.

Du, Xiaofen et al., "Identification of sulphur volatiles and GC-olfactometry aroma profiling in two fresh tomato cultivars" *Food Chemistry*, 2015, vol. 171, pp. 306-314.

Miura, Tsutomu et al., "Platelet Anti-aggregant Activity of 2,2-Dimethylthiazolidine Hydrochloride and 2-(4-Hydroxy-3-methoxyphenyl)thiazolidine," *Chem. Pharm. Bull.*, 1988, vol. 36, No. 3, pp. 1110-1116.

Subedi, Lalita et al., "Neuroprotective and Anti-Inflammatory Activities of Allyl Isothiocyanate through Attenuation of JNK/NF-KB/TNF-a Signaling," *Int. J. Mol. Sci.*, 2017, vol. 18, doi:10.3390/ijms18071423.

Graham, David T. et al. "Vasovagal Fainting: A Diphasic Response," *Psychosomatic Medicine*, vol. 23, No. 6, 1961, pp. 493-507.

Wang et al., "Large-scale forward genetics screening identifies Trpa1 as a chemosensor for predator odor-evoked innate fear behaviors," *Nature Communications*, 2018, 9(1): 2041 (https://www.nature.com/articles/s41467-018-04324-3.pdf), (15 pages).

Isosaka, Tomoko et al., "Htr2a-Expressing Cells in the Central Amygdala Control the Hierarchy between Innate and Learned Fear," *Cell*, Nov. 19, 2015, vol. 163, pp. 1153-1164.

Pereira, Guilherme Alves et al., "A broad study of two new promising antimycobacterial drugs: Ag(I) and Au(I) complexes with 2~(2-thienyl)benzothiazole," *Polyhedron*, 2012, vol. 38, pp. 291-296.

Japanese Patent Office, Communication issued Jul. 9, 2024 in copending Japanese Application No. 2023-117860, with English Translation.

Katsuramaki et al., "Liver Surgery and Nitric Oxide: Inhibition of Ischemia Reperfusion Injury by iNOS Inhibitor", The Sapporo Medical Journal, 2003, vol. 72, pp. 31-36, with English machine translation.

* cited by examiner

PROPHYLACTIC OR THERAPEUTIC AGENT FOR HYPOXIC INJURY, ISCHAEMIA-REPERFUSION INJURY AND INFLAMMATION, CELL PROTECTION AGENT FOR TRANSPLANTATION, AND BIO-PRESERVATION AGENT

CROSS-REFERENCE TO RELATED APPLICATIONS

This application is a Rule 53(b) Continuation of U.S. application Ser. No. 16/981,029 filed Sep. 15, 2020, which is a National Stage of International Application No. PCT/JP2019/010791 filed Mar. 15, 2019, claiming priority based on Japanese Patent Application No. 2018-049761 filed Mar. 16, 2018, the above-noted applications incorporated herein by reference in their respective entireties.

TECHNICAL FIELD

The present invention relates to a prophylactic or therapeutic agent for hypoxic injury, ischemia-reperfusion injury or inflammation, an agent for protecting cells for transplantation, and an agent for preserving organism.

BACKGROUND ART

It is considered that humans and animals have acquired the ability to increase the survival probability when they face risks during the process of evolution. There are many known cases where a human who was lost in a snowy mountain or the like was found in a hypothermic state and recovered even though several hours or longer had elapsed after cardiac arrest. In such cases, it may be that a potential endogenous individual protection action was triggered by some stimulus. Some mammals, such as bear and squirrel, have the ability to hibernate. These animals can sustain life during hibernation in the state with reduced body temperature and reduced oxygen consumption. When oxygen supply stops due to cardiac arrest, cells in tissues with high oxygen demand such as the brain are irreversibly damaged. On the other hand, resumption of blood flow after cardiac arrest causes the generation of active oxygen and the like, which causes great damage to tissues. Such hypoxic injury and ischemia-reperfusion injury are alleviated by therapeutic hypothermia which artificially induces hypothermia in the individual. It is also known that animals in a hibernating state have increased resistance to inflammation, ischemia-reperfusion injury and the like (non-patent documents 1-3).

Fear is an emotion that is triggered when the brain determines that danger is imminent. It causes escape behavior, freezing behavior that reduces the probability of being detected by natural enemies, and the like, and also induces various kinds of physiological responses. When a phobia patient is presented with fear stimuli and faints, the heart rate decreases by nearly 50% (non-patent document 4). Thus, fear emotion is associated with the induction of strong physiological responses also in human. If humans and animals that fell into crisis can enhance the protection action on tissues and individuals by inducing anti-inflammatory and immunoregulatory responses in addition to hypothermia and hypometabolism, survival probability can be increased. However, a technique to induce fear emotionality or potential endogenous individual protection action has not been developed.

DOCUMENT LIST

Patent Document patent document 1: JP-B-5350496

Non-Patent Documents non-patent document 1: N Engl J Med 346:612-613, 2002
non-patent document 2: Lancet Neurol 2: 410-416, 2003
non-patent document 3: Nat Rev Neurosci 13: 267-278, 2012
non-patent document 4: Psychosom Med 23: 493-507, 1961
non-patent document 5: Nature 450: 503-508, 2007
non-patent document 6: Cell 163: 1153-1164, 2015

SUMMARY OF INVENTION

Technical Problem

The present invention aims to provide a technique to induce fear emotionality and potential endogenous individual protection action, and to provide a prophylactic or therapeutic agent for hypoxic injury, ischemia-reperfusion injury or inflammation, an agent for protecting cells for transplantation, and an agent for preserving organism.

Solution to Problem

Fear emotion is controlled by innate and acquired mechanisms. The present inventors have elucidated that the innate and acquired odor information in the nasal cavity is transmitted to the brain by the separated neural circuit and controls the behavior (non-patent document 5). This finding proves the existence of a neural circuit that is responsible for innate behavioral control of odors, and as a result overturns the conventional common sense that behavior for odors is determined by acquired learning and experience. If the response to odors is innately controlled, the development of odor molecules that act on this genetic mechanism may lead to the development of techniques that desirably control behavior. In fact, the present inventors have succeeded for the first time in the world in the development of "thiazoline-related fear odors (tFOs)", which is an artificial odor molecule that induces extremely strong innate fear emotions (patent document 1, non-patent document 6). The development of tFOs has made it possible to elucidate in detail the control mechanism of innate fear emotions, which has been difficult to elucidate heretofore, and the physiological response induced by innate fear emotions.

Both olfactory innate and learned fear stimuli elicited similar levels of freezing behavior. However, using physiological responses as an index, it was clarified that only innate fear stimuli induces a decrease in body temperature and heart rate. Furthermore, it was clarified that hypoxic injury, ischemia-reperfusion injury and inflammation can be suppressed by smelling or intraperitoneally administering a group of compounds (heterocyclic compounds and isothiocyanate compounds) of the present invention which are represented by the following formulas and involved in inducing innate fear or a potential endogenous individual protection action. On the other hand, the present inventors have elucidated that compounds that induce fear emotionality or potential endogenous individual protection action have the property of activating TRPA1 (transient receptor potential ankyrin 1), and that fear emotionality or potential endogenous individual protection action is partially suppressed in TRPA1 knockout mice. These results indicate that a part of the fear emotionality and potential endogenous individual protection action is controlled via the TRPA1 gene. TRPA1 gene is present in a wide range of organisms from mammals such as human and domestic animals to birds, fish and insects for which the prophylactic or therapeutic agent for hypoxic injury, ischemia-reperfusion injury or inflammation, and the agent for protecting cells for transplantation by the technique of the present invention are used.

That is, the present invention relates to the following.

[1] A prophylactic or therapeutic agent for hypoxic injury, ischemia-reperfusion injury or inflammation, an agent for protecting cells for transplantation, or an agent for preserving organism comprising, as an active ingredient, at least one kind selected from a heterocyclic compound represented by the formula (I)

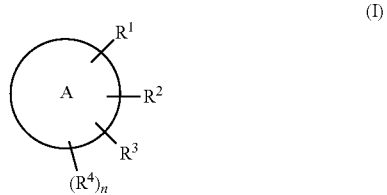

(I)

wherein
ring A is a 5- to 7-membered heterocycle containing 1 or 2 hetero atoms selected from a nitrogen atom, an optionally oxidized sulfur atom and an oxygen atom;
$R^1$, $R^2$, $R^3$ and $R^4$ are each independently a hydrogen atom, a $C_{1-6}$ alkyl group, a halogen atom, an amino group, —SH, a $C_{1-6}$ alkylthio group, a $C_{2-6}$ alkenylthio group, a $C_{1-6}$ alkyl-carbonyl group, a formyl group, a $C_{6-10}$ aryl group, a $C_{1-6}$ alkoxycarbonyl group, a 5- or 6-membered heteroaryl group, or an oxo group;
$R^1$ and $R^2$ are optionally bonded to each other to form an optionally substituted 5- or 6-membered ring; and
n is 0, 1, or 2, or a salt thereof, and
an isothiocyanate compound represented by the formula (II)

$$S=C=N-R^5 \quad (II)$$

wherein $R^5$ is a $C_{1-6}$ alkyl group, a $C_{1-6}$ haloalkyl group, a $C_{2-6}$ alkenyl group, a $C_{6-10}$ aryl group, or a 5- or 6-membered heteroaryl group.

[2] The agent of [1], wherein the ring A is thiazoline, thiazole, thiazolidine, thiomorpholine, thiophene, pyrrole, morpholine, azepane, pyridine, pyrazine, furan, 2,3-dihydro-4H-1,4-thiazine, or imidazole.

[3] The agent of [1] or [2], wherein the active ingredient is a heterocyclic compound represented by the formula (I) or a salt thereof.

[4] The agent of [1], wherein the active ingredient is an isothiocyanate compound represented by the formula (II).

[5] The agent of any one of [1] to [4], wherein the agent is a prophylactic or therapeutic agent for hypoxic injury, ischemia-reperfusion injury or inflammation.

[6] The agent of any one of [1] to [4], wherein the agent is an agent for protecting cells for transplantation.

[7] The agent of any one of [1] to [4], wherein the agent is an agent for preserving organism.

[8] The agent of any one of [1] to [7], wherein the agent is for intranasal administration.

[9] A prophylactic or therapeutic agent for hypoxic injury, ischemia-reperfusion injury or inflammation, comprising a TRPA1 agonist as an active ingredient.

[10] An agent for protecting cells for transplantation, comprising a TRPA1 agonist as an active ingredient.

[11] An agent for preserving organism comprising a TRPA1 agonist as an active ingredient.

[12] The agent of any one of [9] to [11], wherein the agent is for intranasal administration.

[13] At least one kind of compound selected from a heterocyclic compound represented by the aforementioned formula (I) or a salt thereof, and an isothiocyanate compound represented by the aforementioned formula (II) for use in the prophylaxis or treatment of hypoxic injury, ischemia-reperfusion injury or inflammation.

[14] Use of at least one kind of compound selected from a heterocyclic compound represented by the aforementioned formula (I) or a salt thereof, and an isothiocyanate compound represented by the aforementioned formula (II) as an agent for protecting cells for transplantation or an agent for preserving organism.

[15] A TRPA1 agonist for use in the prophylaxis or treatment of hypoxic injury, ischemia-reperfusion injury or inflammation.

[16] Use of a TRPA1 agonist as an agent for protecting cells for transplantation or an agent for preserving organism.

[17] Use of at least one kind of compound selected from a heterocyclic compound represented by the aforementioned formula (I) or a salt thereof, and an isothiocyanate compound represented by the aforementioned formula (II) for producing a prophylactic or therapeutic agent for hypoxic injury, ischemia-reperfusion injury or inflammation, an agent for protecting cells for transplantation, or an agent for preserving organism.

[18] Use of a TRPA1 agonist for producing a prophylactic or therapeutic agent for hypoxic injury, ischemia-reperfusion injury or inflammation, an agent for protecting cells for transplantation, or an agent for preserving organism.

[19] A method for preventing or treating hypoxic injury, ischemia-reperfusion injury or inflammation in a mammal, comprising administering an effective amount of at least one kind of compound selected from a heterocyclic compound represented by the aforementioned formula (I) or a salt thereof, and an isothiocyanate compound represented by the aforementioned formula (II) to the mammal.

[20] A method for protecting cells for transplantation, comprising contacting the cells for transplantation with at least one kind of compound selected from a heterocyclic compound represented by the aforementioned formula (I) or a salt thereof, and an isothiocyanate compound represented by the aforementioned formula (II).

[21] A method for preserving an organism, comprising contacting the organism with at least one kind of compound selected from a heterocyclic compound represented by the aforementioned formula (I) or a salt thereof, and an isothiocyanate compound represented by the aforementioned formula (II).

[22] A method for preventing or treating hypoxic injury, ischemia-reperfusion injury or inflammation in a mammal, comprising administering an effective amount of a TRPA1 agonist to the mammal.

[23] A method for protecting cells for transplantation, comprising contacting the cells for transplantation with a TRPA1 agonist.

[24] A method for preserving an organism, comprising contacting the organism with a TRPA1 agonist.

Advantageous Effects of Invention

Fear is an emotion induced by the brain that has sensed a dangerous situation and induces behaviors and physiological responses that increase the survival probability of survival in humans and animals in danger. Therapeutic hypothermia that artificially lowers body temperature and metabolism has the effect of improving the prognosis of emergency patients. Therefore, the function of the brain, nervous system and the like that have sensed fear and danger signals to acquire tissue and individual protection action by inducing decline of systemic body temperature and metabolism, and controlling inflammation and immune response is purposeful. However, the mechanism that controls such fear emotionality and potential endogenous individual protection action has not been elucidated. The technique of the present invention confers strong resistance to hypoxic injury, ischemia-reperfusion injury, and inflammation by the administration of a compound satisfying particular chemical structural requirements, simultaneously with induction of a behavior that characterizes innate fear and potential endogenous individual protection action and physiological responses such as the hypothermia, hypometabolism and the like, and suppression of inflammation and immune responses. The compound utilized in the technique of the present invention exhibits the effect by a method of activating the receptor by volatilized odor molecules or incorporating the compound into the body, or a method of directly administering the compound to the body by injection or the like. The effects thereof include induction of hypothermia, hypometabolism, suppression of oxygen consumption, low heart rate, anti-inflammatory reaction, protection action on tissues and individuals under hypoxic conditions, protection action against ischemia-reperfusion injury, protection action against inflammation and the like. By this technique, a therapeutic drug for hypoxic injury, ischemia-reperfusion injury or inflammation in individuals, an agent for protecting organs for transplantation, and an agent for preserving organism can be provided.

DESCRIPTION OF EMBODIMENTS

Figure 1:
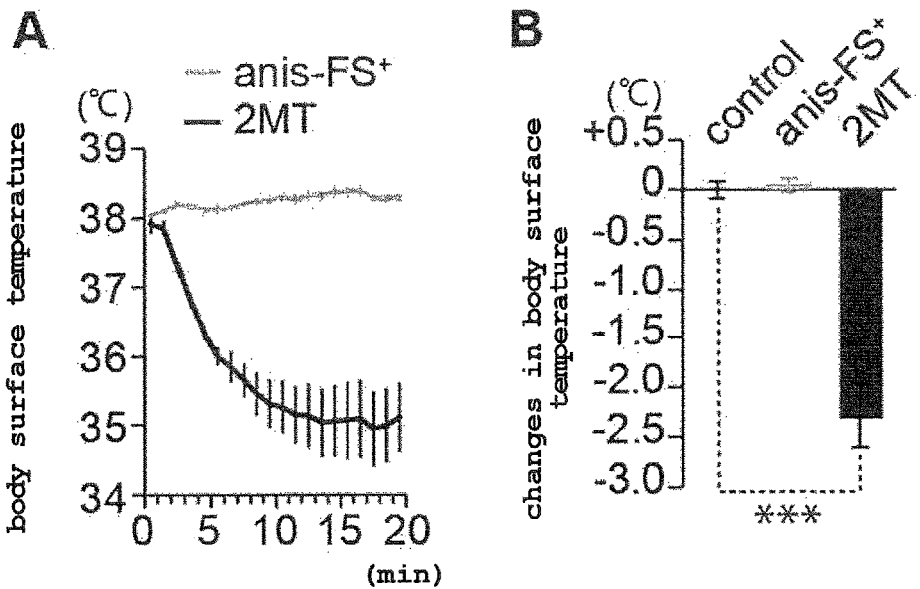
FIG. 1 A: Figure showing time-course changes (mean±standard error) in the body surface temperature when 2MT (2-methyl-2-thiazoline) or an odor molecule that induces learned fear (anis-FS$^+$) was smelled. B: Figure showing mean changes in the body surface temperature for 20 min when 2MT or an odor molecule that induces learned fear (anis-FS$^+$) was presented.

The ring A in the formula (I) is a 5- to 7-membered heterocycle containing 1 or 2 hetero atoms selected from a nitrogen atom, an optionally oxidized sulfur atom and an oxygen atom. The ring A is preferably a 5- to 7-membered heterocycle containing 1 or 2 hetero atoms selected from a nitrogen atom and an optionally oxidized sulfur atom. The ring A is more preferably a 5- to 7-membered heterocycle containing a nitrogen atom and an optionally oxidized sulfur atom. The number of members of ring A is more preferably 5 or 6.

Examples of the aforementioned heterocycle includes, but are not limited to, pyrrole, pyridine, pyridazine, pyrimidine, pyrazine, piperazine, pyrrolidine, hexahydropyridazine, imidazole, imidazolidine, piperidine, thiophene, thiolane, tetrahydro-2H-thiopyran, thiazoline (e.g., 2-thiazoline, 3-thiazoline, 4-thiazoline), thiazole, thiazolidine, isothiazole, isothiazoline, thiomorpholine, thiadiazoline, thiadiazole, thiadiazolidine, 1,3-thiazinane, 5,6-dihydro-4H-1,3-thiazine, 2,3-dihydro-4H-1,4-thiazine, furan, 2H-pyran, 4H-pyran, oxazole, isoxazole, morpholine, oxazoline, azepane and the like. It is preferably thiazoline (e.g., 2-thiazoline, 3-thiazoline, 4-thiazoline), thiazole, thiazolidine, thiomorpholine, thiophene, pyrrole, morpholine, azepane, pyridine, pyrazine, furan, 2,3-dihydro-4H-1,4-thiazine, or imidazole, further preferably thiazoline (e.g., 2-thiazoline), thiazole, thiazolidine, thiomorpholine, thiophene, or 2,3-dihydro-4H-1,4-thiazine.

The "halogen atom" used here is preferably selected from a fluorine atom, a chlorine atom, a bromine atom and an iodine atom.

The "$C_{1-6}$ alkyl group" used here (when used as a group or a part of a group) is a straight chain or branched chain alkyl group having 1 to 6 carbon atoms. Examples of the $C_{1-6}$ alkyl group include, but are not limited to, methyl group, ethyl group, propyl group, isopropyl group, butyl group, 1-methylpropyl group (sec-butyl group), 2-methylpropyl group (isobutyl group), tert-butyl group, pentyl group, 1-methylbutyl group, 2-methylbutyl group, 3-methylbutyl group, 1,1-dimethylpropyl group, 2,2-dimethylpropyl group, 1,2-dimethylpropyl group, 1-ethylpropyl group, hexyl group, 1-methylpentyl group, 2-methylpentyl group, 3-methylpentyl group, 4-methylpentyl group, 1,1-dimethylbutyl group, 2,2-dimethylbutyl group, 3,3-dimethylbutyl group, 1,2-dimethylbutyl group, 1,3-dimethylbutyl group, 2,3-dimethylbutyl group, 1-ethylbutyl group, 2-ethylbutyl group, 1-ethyl-2-methylpropyl group and the like. Preferable examples of the $C_{1-6}$ alkyl group include $C_{1-4}$ alkyl group (straight chain or branched chain alkyl group having 1-4 carbon atoms). It is further preferably methyl group, ethyl group, propyl group, isopropyl group, butyl group, isobutyl group, or sec-butyl group, and particularly preferably methyl group.

The "$C_{1-6}$ haloalkyl group" used here means a $C_{1-6}$ alkyl group substituted by 1 to 5 halogeno groups. When two or more halogeno groups are present, the kind of respective halogeno groups may be the same or different. As the halogeno group, a fluoro group, a chloro group, a bromo group and the like can be mentioned. Examples of the $C_{1-6}$ haloalkyl group include, but are not limited to, fluoromethyl group, difluoromethyl group, trifluoromethyl group, chlorodifluoromethyl group, 1-fluoroethyl group, 2-fluoroethyl group, 2-chloroethyl group, 2-bromoethyl group, 1,1-difluoroethyl group, 1,2-difluoroethyl group, 2,2,2-trifluoroethyl group, 1,1,2,2-tetrafluoroethyl group, 1,1,2,2,2-pentafluoroethyl group, 1-fluoropropyl group, 1,1-difluoropropyl group, 2,2-difluoropropyl group, 3-fluoropropyl group, 3,3,3-trifluoropropyl group, 4-fluorobutyl group, 4,4,4-trifluorobutyl group, 5-fluoropentyl group, 5,5,5-trifluoropentyl group, 6-fluorohexyl group, 6,6,6-trifluorohexyl group and the like.

The "$C_{2-6}$ alkenyl group" used here (when used as a group or a part of a group) means a straight chain or branched chain alkenyl group having 2 to 6 carbon atoms. Examples of the $C_{2-6}$ alkenyl group include, but are not limited to, vinyl group, allyl group, prop-1-enyl group, but-1-en-1-yl group, but-2-en-1-yl group, pent-4-en-1-yl group, 2-methylallyl group and the like.

The "$C_{1-6}$ alkoxy group" used here (when used as a group or a part of a group) means a straight chain or branched chain alkoxy group having 1 to 6 carbon atoms. Examples of the $C_{1-6}$ alkoxy group include, but are not limited to, methoxy group, ethoxy group, propoxy group, isopropoxy group, butoxy group, 1-methylpropoxy group, 2-methylpropoxy group, tert-butoxy group, pentyloxy group, 1-methylbutoxy group, 2-methylbutoxy group, 3-methylbutoxy group, 1,1-dimethylpropoxy group, 2,2-dimethylpropoxy group, 1,2-dimethylpropoxy group, 1-ethylpropoxy group, hexyloxy group, and the like.

The "$C_{1-6}$ alkylthio group" used here means an —SH group substituted by a $C_{1-6}$ alkyl group. Examples of the $C_{1-6}$ alkylthio group include, but are not limited to, methylthio group, ethylthio group, propylthio group, butylthio group and the like.

The "$C_{2-6}$ alkenylthio group" used here means an —SH group substituted by $C_{2-6}$ alkenyl. Examples of the $C_{2-6}$ alkenylthio group include, but are not limited to, vinylthio group, allylthio group, prop-1-enylthio group, but-1-en-1-ylthio group, but-2-en-1-ylthio group, pent-4-en-1-ylthio group, 2-methylallylthio group and the like.

The "$C_{1-6}$ alkyl-carbonyl group" used here means a carbonyl group bonded to a $C_{1-6}$ alkyl group. Examples of the $C_{1-6}$ alkyl-carbonyl group include, but are not limited to, acetyl group, propionyl group, butyryl group, isobutyryl group, valeryl group, hexanoyl group and the like.

The "$C_{1-6}$ alkoxycarbonyl group" used here means a carbonyl group bonded to a $C_{1-6}$ alkoxy group. Examples of the $C_{1-6}$ alkoxycarbonyl group include, but are not limited to, methoxycarbonyl group, ethoxycarbonyl group, propoxycarbonyl group, isopropoxycarbonyl group, butoxycarbonyl group and the like.

The "$C_{6-10}$ aryl group" used here means an aromatic hydrocarbon group having 6 to 10 carbon atoms. Examples of the $C_{6-10}$ aryl group include, but are not limited to, phenyl group, naphthyl group (1-naphthyl group, 2-naphthyl group) and the like.

The "5- or 6-membered heteroaryl group" used here means a 5- or 6-membered heteroaryl group containing at least 1 (preferably 1 to 3, more preferably 1 or 2) hetero atom selected from nitrogen atom, optionally oxidized sulfur atom and oxygen atom. The 5- or 6-membered heteroaryl group is preferably a 5- or 6-membered heteroaryl group containing 1 or 2 hetero atoms selected from nitrogen atom and optionally oxidized sulfur atom.

Examples of the 5- or 6-membered heteroaryl group include, but are not limited to, pyrrolyl group, pyridyl group, pyridazinyl group, pyrimidinyl group, pyrazinyl group, imidazolyl group, thienyl group, thiazolyl group, isothiazolyl group, thiadiazolyl group, furyl group, oxazolyl group, isoxazolyl group and the like. Preferably, it is pyridyl group, thienyl group and the like.

The term "oxo group" used here (when used as a group or a part of a group) shows an =O group.

The term "optionally oxidized sulfur atom" used here means S, SO, or $SO_2$.

The "5- or 6-membered ring" of the "optionally substituted 5- or 6-membered ring" formed by $R^1$ and $R^2$ bonded to each other means a 5- or 6-membered ring containing at least 1 (preferably 1 to 3, more preferably 1 or 2) hetero atom selected from nitrogen atom, optionally oxidized sulfur atom and oxygen atom. Examples of the aforementioned 5- or 6-membered ring include benzene ring, tetrahydropyrimidine ring and the like. The aforementioned 5- or 6-membered ring may be substituted, and examples of the substituent include 1 to 4 (preferably 1 or 2) substituents selected from $C_{1-6}$ alkyl group, halogen atom, amino group, —SH, $C_{1-6}$ alkylthio group, $C_{2-6}$ alkenylthio group, $C_{1-6}$ alkylcarbonyl group, formyl group, $C_{1-6}$ alkoxycarbonyl group, oxo group and the like. The substituent is preferably 1 to 4 substituents selected from $C_{1-6}$ alkyl group (e.g., methyl) and oxo group.

In the formula (I), preferably, $R^1$, $R^2$, $R^3$ and $R^4$ are each independently hydrogen atom, $C_{1-6}$ alkyl group (e.g., methyl, ethyl, propyl, isopropyl, butyl, isobutyl, sec-butyl), halogen atom (e.g., chlorine atom), amino group, —SH, $C_{1-6}$ alkylthio group (e.g., methylthio), $C_{2-6}$ alkenylthio group (e.g., allylthio), $C_{1-6}$ alkyl-carbonyl group (e.g., acetyl), formyl group, $C_{6-10}$ aryl group (e.g., phenyl), 5- or 6-membered heteroaryl group (e.g., thienyl), or oxo group; and $R^1$ and $R^2$ are optionally bonded to each other to form an optionally substituted 5- or 6-membered ring (e.g., benzene ring, tetrahydropyrimidine ring).

In the formula (I), when n=1 or 2, it is preferable that at least one of $R^1$, $R^2$, $R^3$ and $R^4$ is not a hydrogen atom. In the formula (I), when n=0, it is preferable that at least one of $R^1$, $R^2$ and $R^3$ is not a hydrogen atom.

Examples of the preferable heterocyclic compound of the formula (I) used as the active ingredient in the present invention include, but are not limited to, 2-methyl-2-thiazoline (2MT),
2,4,5-trimethylthiazole,
2-aminothiazole,
thiomorpholine,
2-ethylpyrrole,
2-acetylthiophene,
3-chlorothiophene,
2,3-dimethylthiomorpholine,
2,6-dimethylthiomorpholine,
2-methylthiomorpholine,
2-(methylthio)-2-thiazoline,
2-methylthiophene,
2-sec-butyl-2-thiazoline (SBT),
4-ethyl-2-methyl-2-thiazoline (4E2MT),
2-amino-2-thiazoline,
2-ethylthiophene,
2,4,5-trimethyl-3-thiazoline (TMT),
2-methylthiazole,
3-methylpyrrole,
thiomorpholine 1,1-dioxide,
2-isopropyl-4-methylthiazole,
azepane,
2,6-dimethylpyridine (2,6-lutidine),
2-ethyl-4-methylthiazole,
2-mercaptothiazole,
thiazole,
2,4-dimethylpyridine,
2-propylthiazole,
4-phenylthiomorpholine 1,1-dioxide,
2-(allylthio)-2-thiazoline,
5-methylthiazole,
thiazolidine,
2-methylbenzo[d]thiazole,
2-chlorothiazole,
2,4-dimethyl-1H-pyrrole,
caffeine,
2-acetylthiazole,
2,3-diethylpyrazine,
2-isobutylthiazole,
2-(2-thienyl)benzothiazole,
3,4-dimethylpyridine,
2-ethylfuran,
3-methylthiophene, 2H-1,4-benzothiazine-3(4H)-one,
5-thiazolecarboxaldehyde (5-formylthiazole),
2,6-dimethylpyrazine,
2,2-dimethylthiazolidine,
2,3-dimethylpyridine,
3-methylpyridine,
morpholine,
2-thiophenecarboxaldehyde,
2,5-dimethyl-2-thiazoline,
2-ethyl-2-thiazoline
2-ethyl-3,5-dimethylpyrazine
and the like.

Examples of the preferable isothiocyanate compound of the formula (II) used as the active ingredient in the present invention include, but are not limited to,
methallyl isothiocyanate,
allyl isothiocyanate,
ethyl isothiocyanate,
2-chloroethyl isothiocyanate,
3-pyridyl isothiocyanate,
phenyl isothiocyanate,
4-penten-1-yl isothiocyanate,
butyl isothiocyanate,
propyl isothiocyanate
and the like.

In the present invention, the TRPA1 agonist is a substance that activates TRPA1. In the present invention, examples of the preferable TRPA1 agonist used as the active ingredient include, but are not limited to,
5-methylthiazole,
2-ethylfuran,
4-ethyl-2-methyl-2-thiazoline,
2-methylthiophene,
2,3-diethylpyrazine,
2-ethyl-3,5-dimethylpyrazine,
2-acetylthiophene,
2,6-lutidine (2,6-dimethylpyridine),
thiomorpholine,
acetaminophen,
allyl isothiocyanate,
Δ9-tetrahydrocannabinol
and the like.

In the present invention, a heterocyclic compound of the formula (I) and an isothiocyanate compound of the formula (II) used as the active ingredients include substances generally known as reagents, commercially available ones can be utilized, and they can be obtained by a method known per se. Use of the heterocyclic compound of the formula (I) and the isothiocyanate compound of the formula (II) as prophylactic or therapeutic agents for hypoxic injury, ischemia-reperfusion injury or inflammation, agents for protecting cells for transplantation, or agents for preserving organism has not been disclosed or suggested to date.

Preferable examples of the heterocyclic compound represented by the formula (I) include compounds represented by the following formulas (A)-(D) or salts thereof.

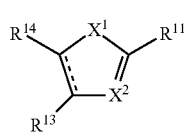

(A)

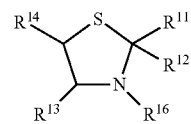

(B)

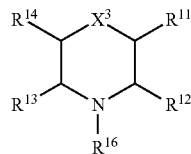

(C)

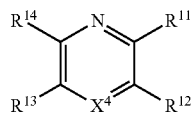

(D)

wherein
$X^1$ is S, O, or $N(R^{16})$;
$X^2$ is N or $CR^{12}$;
$X^3$ is S, $SO_2$, O, or $—(CH_2)_2—$;
$X^4$ is N or $CR^{15}$;

------ is a single bond or a double bond;
$R^{11}$, $R^{12}$, $R^{13}$, $R^{14}$, $R^{15}$ and $R^{16}$ are each independently a hydrogen atom, a $C_{1-6}$ alkyl group, a halogen atom, an amino group, —SH, a $C_{1-6}$ alkylthio group, a $C_{2-6}$ alkenylthio group, a $C_{1-6}$ alkyl-carbonyl group, a formyl group, a $C_{6-10}$ aryl group, a $C_{1-6}$ alkoxycarbonyl group, a 5- or 6-membered heteroaryl group, or an oxo group; $R^{13}$ and $R^{14}$ are optionally bonded to each other to form a benzene ring, or a tetrahydropyrimidine ring optionally substituted by 1 to 4 substituents selected from a $C_{1-6}$ alkyl group and an oxo group; provided that, in the formula (A), $R^{11}$ and $R^{12}$ are not oxo groups; in the formula (A), when

------ is a double bond, $R^{13}$ and $R^{14}$ are not oxo groups;
in the formula (D), $R^{11}$, $R^{12}$, $R^{13}$, $R^{14}$ and $R^{15}$ are not oxo groups, in the formula (B), and $R^{11}$ and $R^{12}$ may together form an oxo group.

In the formulas (A) to (D), preferably, $R^{11}$, $R^{12}$, $R^{13}$, $R^{14}$, $R^{15}$ and $R^{16}$ are each independently a hydrogen atom, a $C_{1-6}$ alkyl group (e.g., methyl, ethyl, propyl, isopropyl, butyl, isobutyl, sec-butyl), halogen atom (e.g., chlorine atom), an amino group, —SH, a $C_{1-6}$ alkylthio group (e.g., methylthio), a $C_{2-6}$ alkenylthio group (e.g., allylthio), a $C_{1-6}$ alkyl-carbonyl group (e.g., acetyl), a formyl group, a $C_{6-10}$ aryl group (e.g., phenyl), a 5- or 6-membered heteroaryl group (e.g., thienyl), or an oxo group; $R^{13}$ and $R^{14}$ are optionally bonded to each other to form a benzene ring, or a tetrahydropyrimidine ring optionally substituted by 1 to 4 substituents selected from a $C_{1-6}$ alkyl group and an oxo group.

The salt of the compound of the present invention may be a pharmaceutically acceptable salt. For example, alkali metal salts such as sodium salt and potassium salt; alkaline earth metal salts such as magnesium salt and calcium salt; ammonium salts such as dimethylammonium salt and triethylammonium salt; inorganic acid salts such as hydrochloride, perchlorate, sulfate and nitrate; organic acid salts such as acetate and methanesulfonate; and the like can be mentioned.

In the present invention, hypoxic injury refers to a disease caused by hypoxia. For example, hypoxia, hypoxic encephalopathy, neonatal hypoxia, hypoxic-ischemic encephalopathy, hypoxic hypoxia, ischemic hypoxia, stagnant hypoxia, altitude sickness, cerebral infarction, myocardial infarction, renal failure, cardiac failure, diabetic angiopathy, arteriosclerosis obliterans, ulcer, spinal cord injury, optic neuropathy, photoreceptor cell injury, neuropathy and the like can be mentioned.

In the present invention, ischemia-reperfusion injury refers to a disorder in cells and tissues of the ischemic organ caused by reperfusion associated with resumption of blood flow to the organ in an ischemic state. For example, ischemia-reperfusion injury after reperfusion therapy for myocardial infarction, cerebral infarction, mesenteric vascular occlusion and the like or after organ transplantation; pressure ulcer and the like can be mentioned.

In the present invention, inflammation refers to a pathological inflammatory condition in the whole body or tissues that is induced by trauma, pathogen invasion, chemical substance stimulation, radiation injury and the like. For example, sepsis, encephalitis, meningitis, arteritis, sinusitis, rhinitis, pneumonia, bronchitis, stomatitis, esophagitis, gastritis, enteritis, hepatitis, myositis, dermatitis, arthritis, nephritis, adrenalitis, lymphangitis, rheumatoid arthritis, psoriasis, osteoporosis, Crohn's disease and the like can be mentioned.

In the present invention, the agent for protecting cells for transplantation refers to an agent used for protecting cells for transplantation (including organ, tissue). Examples of the cell include organs and tissues such as heart, lung, kidney, liver, bone marrow, pancreas, skin, bone, vein, artery, cornea, blood vessel, small intestine, large intestine, brain, spinal cord, smooth muscle, skeletal muscle, ovary, testis, uterus, umbilical cord and the like, and cells derived therefrom.

In the present invention, the agent for preserving organism can be used for preserving the whole body or a part of an organism and maintaining its freshness when storing or transporting the organism as a food. Examples of the organism include organisms such as animals and plants, fish and shellfish and the like used as foods. In the present invention, organism refers to whole body or a part of an organism such as animals and plants, fish and shellfish and the like (e.g., fish, shellfish, farm animals, vegetables, fruits and the like) used as foods.

The heterocyclic compound represented by the aforementioned formula (I) or a salt thereof, or the isothiocyanate compound represented by the aforementioned formula (II) (hereinafter to be also referred to as the compound of the present invention) can be utilized as a prophylactic or therapeutic agent for hypoxic injury, ischemia-reperfusion injury or inflammation by vaporizing and inhaling, or intracorporeally administering the compound. Alternatively, the compound of the present invention can be utilized as an agent for protecting cells for transplantation by administering the compound to a donor to remove organ for transplantation from, or adding the compound to a preservation solution for an isolated organ for transplantation (including tissue, cell). It can also be utilized as an agent for preserving organism by adding the compound to a preservation solution for animals and plants, fish and shellfish, and the like used as foods.

Administration Method

The compound of the present invention can be administered to animals, including a human who has or may develop hypoxic injury, ischemia-reperfusion injury or inflammation in an attempt to prevent development of injury or alleviate symptoms. In addition, the compound of the present invention can be intracorporeally administered to a donor of organ transplantation for the purpose of tissue protection. A gas derived from the compound of the present invention and developed at a concentration of 0.1 to 100,000 ppm (or 10 to 100,000 ppm) can be inhaled through nasal cavity or lung using a gas mask or a device having a similar function. Alternatively, the compound of the present invention can be administered orally at a dose of 1 μg/kg to 5,000 mg/kg. Alternatively, the compound of the present invention can be intracorporeally injected at a dose of 1 μg/kg to 5,000 mg/kg by a method such as intradermal injection, subcutaneous injection, intramuscular injection, intravenous injection, intraarterial injection, intraspinal injection, intraperitoneal injection and the like. The administration frequency may be single-dose administration, or continuous administration at regular intervals, or continuous administration at different time intervals. When the agent for protecting cells for transplantation of the present invention is added to a preservation solution for organ (including tissue, cell) for transplantation, the concentration of the compound of the present invention in the preservation solution is preferably 1 μg/l to 5,000 mg/l. The animal to be the subject of administration or organ transplantation donor may be, for example, mammals (human, mouse, rat, hamster, rabbit, cat, dog, bovine, sheep, swine, horse, monkey and the like). When the agent for protecting organism of the present invention is added to a preservation solution during storage and transportation of foods, the concentration of the compound of the present invention in the preservation solution is preferably 1 μg/l to 5,000 mg/l. The organism to be the administration subject includes mammals, fish, birds, and insects.

When the compound of the present invention is used as a prophylactic or therapeutic agent for hypoxic injury or ischemia-reperfusion injury or inflammation, an agent for protecting cells for transplantation, or an agent for preserving organism (hereinafter to be also referred to as the agent of the present invention), a pharmaceutically acceptable additive can be added as necessary. That is, the agent of the present invention can be used as a composition (pharmaceutical composition) containing the compound of the present invention and a pharmaceutically acceptable additive.

Specific examples of the pharmaceutically acceptable additive include, but are not limited to, antioxidant, preservative, colorant, flavoring agent, and diluent, emulsifier, suspending agent, solvent, filler, extending agent, buffering agent, delivery vehicle, diluent, carrier, excipient and/or pharmaceutical adjuvant and the like.

The dosage form of the agent of the present invention is not particularly limited and, for example, liquid, injection, sustained-release preparation, spray and the like can be mentioned. The solvent to be used for formulating the agent of the present invention in the above-mentioned dosage form may be aqueous or non-aqueous.

An injection can be prepared by a method well known in the pertinent field. For example, an injection can be prepared by dissolving in an appropriate solvent (saline, buffer such as PBS, sterile water and the like), sterilizing by filtration with a filter or the like, and then filling in an aseptic container (e.g., ampoule and the like). The injection may contain a conventionally-used pharmacological carrier as necessary. An administration method using a non-invasive catheter can also be adopted. The carrier that can be used in the present invention includes neutral buffered saline, saline containing serum albumin, and the like.

The present invention is explained in more detail in the following by referring to Examples and Experimental Examples. The Examples and Experimental Examples do not limit the present invention.

EXAMPLES

Example 1: Body Surface Temperature Decrease Induced by Thiazoline-Related Compound Experiment Method An influence of a thiazoline-related compound and an odor molecule that induces learned fear on the body surface temperature was analyzed. Male C57/BL6N mice (about 3 months old) were anesthetized with pentobarbital (50 mg/kg, i.p.) 2-3 days before the test, and the back hair was depilated with depilatory cream. On the day of testing, each mouse was placed in a test cage and, after acclimation for 10 min, a filter paper scented with 271 μmol of a thiazoline-related compound (2-methyl-2-thiazoline; 2MT) or an odor molecule that induces learned fear (anisole) was presented in the test cage, and changes in the body surface temperature on the back were analyzed using a thermography camera (NEC Avio). The value of the body surface temperature change was calculated as the difference between the mean body surface temperature for 10 min when water was presented and the mean body surface temperature for 20 min when each odor molecule was presented, and the change in the body surface temperature without odor was set to 0. The mice presented with the odor that induces learned fear were trained to associate the anisole odor with electric shock one day before the test day, whereby the mice learned to feel learned fear against the smell of anisole.

Results

The results are shown in FIG. 1.

FIG. 1A shows time-course changes (mean±standard error) in the body surface temperature when thiazoline-related compound (2MT) or an odor molecule that induces learned fear (anis-FS$^+$) was smelled (n≥8).

FIG. 1B shows mean changes in the body surface temperature for 20 min when thiazoline-related compound (2MT) or an odor molecule that induces learned fear (anis-FS$^+$) was presented. The graph shows the values of mean±standard error, and Student's t-test was performed on the changes in the body surface temperature without odor and when odor was presented. *** means the presence of a significant difference at p<0.001.

The thiazolin-related compound (2MT) that induces innate fear caused a clear decrease in the body surface temperature. In contrast, the odor molecule (anis-FS+) that induces learned fear did not show a significant influence on the body surface temperature.

Example 2: Body Surface Temperature Decrease Induced by Various Thiazoline-Related Compounds Experiment Method An influence of various thiazoline-related compounds on the body surface temperature was analyzed by a method similar to that in Example 1. As a control, an influence of an odor molecule that induces learned fear was also analyzed.
experiment compound (notation in FIG. 2 is shown in parentheses)
2-methyl-2-thiazoline (2-methylthiazoline)
2,5-dimethyl-2-thiazoline (2,5-dimethylthiazoline)
2,2-dimethylthiazolidine (2,2-dimethylthiazolidine)
2,4,5-trimethyl-3-thiazoline (TMT)
thiazole (Thiazole)
2-ethyl-2-thiazoline (2-ethylthiazoline)
thiomorpholine (thiomorpholine)

Results

Figure 2:
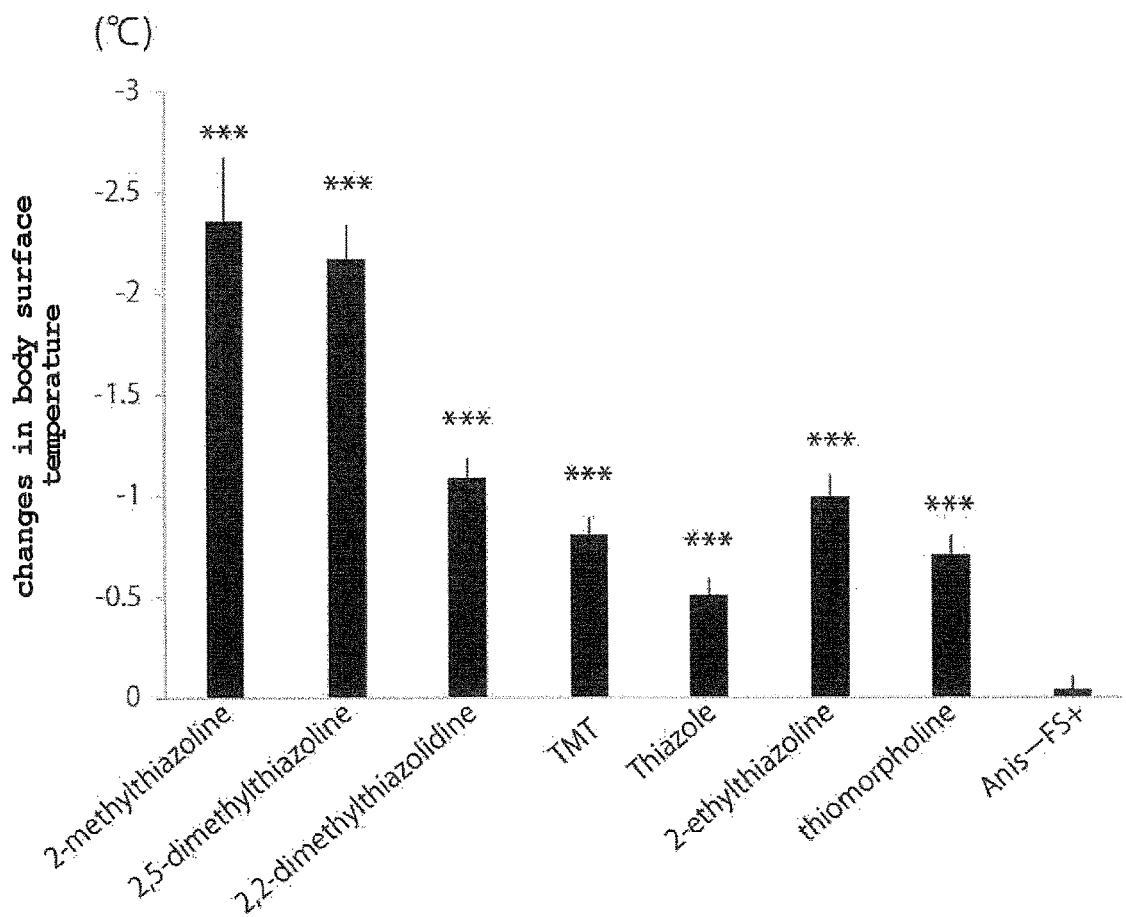
FIG. 2 shows mean changes in the body surface temperature when various kinds of thiazoline-related compounds or an odor molecule that induces learned fear (Anis-FS$^+$) were/was presented.

The results are shown in FIG. 2.

FIG. 2 shows mean changes in the body surface temperature when various kinds of thiazoline-related compounds or an odor molecule that induces learned fear (Anis-FS$^+$) were/was presented. The graph shows the values of mean±standard error, and Student's t-test was performed on the changes in the body surface temperature when an odor molecule that induces learned fear and a thiazoline-related compound were presented. *** means the presence of a significant difference at p<0.001 (each n≥8).

It was shown that various kinds of thiazoline-related compounds exhibit an effect of significantly lowering the body surface temperature.

Figure 3:
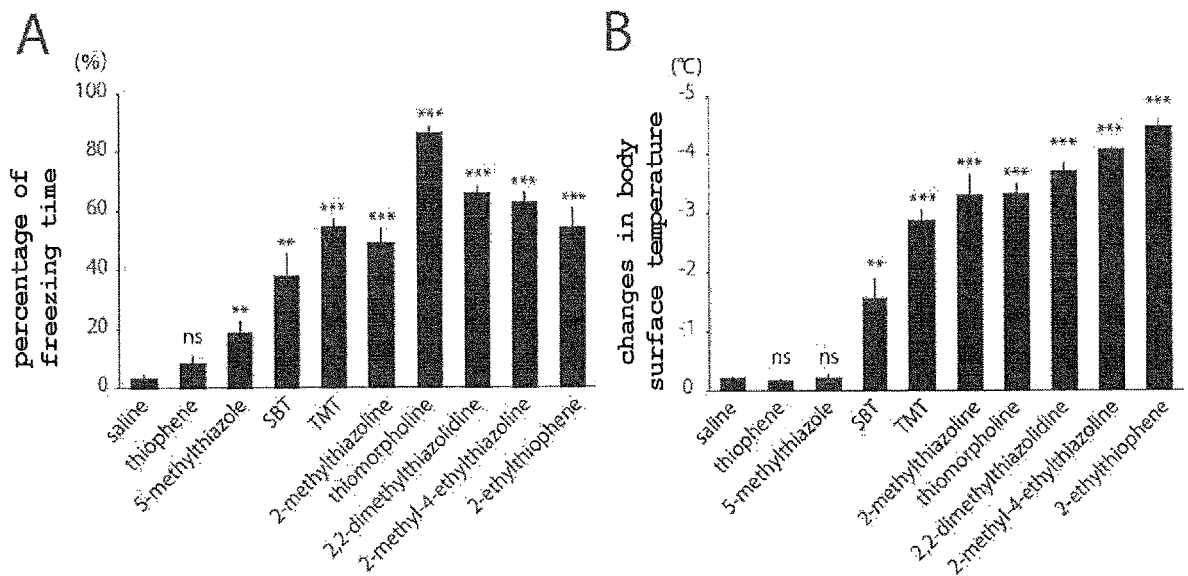
FIG. 3 A: Figure showing mean±standard error of freezing behavior when various kinds of thiazoline-related compounds were intraperitoneally injected. B: Figure showing mean±standard error of changes in the body surface temperature when various kinds of thiazoline-related compounds were intraperitoneally injected.

Example 3: Freezing Behavior and Decrease in Body Surface Temperature Induced by Intraperitoneal Administration of Various Thiazoline-Related Compounds Experiment Method Influence of intraperitoneal administration of various kinds of thiazoline-related compounds on the freezing behavior (freezing time) and body surface temperature of mice was analyzed. The odor molecule was administered by a method of intraperitoneally injecting 100 μl (about 40 mg/kg, i.p.) of a solution diluted 100 times with saline, and the body surface temperature was measured by a method similar to that in Example 1. The freezing behavior was measured using freezing behavior analysis software (Freeze Frame2) and calculated as the percentage (%) of freezing time during 20 min after odor molecule administration. As a control, the freezing behavior and changes in the body surface temperature by intraperitoneal administration of saline and an odor molecule (thiophene) that does not induce innate fear were also analyzed.
Experiment compound (notation in FIG. 3 is shown in parentheses) thiophene (thiophene)
5-methylthiazole (5-methylthiazole)
2-sec-butyl-2-thiazoline (SBT)
2,4,5-trimethyl-3-thiazoline (TMT)
2-methyl-2-thiazoline (2-methylthiazoline)
thiomorpholine (thiomorpholine)
2,2-dimethylthiazolidine (2,2-dimethylthiazolidine)
2-methyl-4-ethyl-2-thiazoline (2-methyl-4-ethylthiazoline)
2-ethylthiophene (2-ethylthiophene)
Results The results are shown in FIG. 3.

FIG. 3A shows mean±standard error of freezing behavior when various kinds of thiazoline-related compounds were intraperitoneally injected. As a control, the freezing behavior without an odor (saline) was analyzed, and Student's t-test was performed on the freezing behavior with or without odor.  means the presence of a significant difference at p<0.01, * at p<0.001, and ns means no significant difference at p>0.05.

FIG. 3B shows mean±standard error of changes in the body surface temperature when various kinds of thiazoline-related compounds were intraperitoneally injected. As a control, changes in the body surface temperature without an odor (saline) were analyzed, and Student's t-test was performed on the changes in the body surface temperature with or without odor.  means the presence of a significant difference at p<0.01, * at p<0.001, and ns means no significant difference at p>0.05.

Intraperitoneal administration of a thiazoline-related compounds induced freezing behavior. Also, the intraperitoneal administration of various kinds of thiazoline-related compounds induced a decrease in the body surface temperature.

Example 4: Core Body Temperature Decrease Induced by Thiazoline-Related Compound Experiment Method An influence of a thiazoline-related compound and an odor molecule that induces learned fear on the core body temperature was analyzed. A radio-telemetry device for monitoring biological parameters (manufactured by Physiotel) was surgically implanted in the abdomen of male C57/BL6N mice (about 3 months old). The mice were subjected to the following experiment after about 10 days of recovery period. Each mouse was placed in a test cage and, after acclimation for 10 min, a filter paper dropped with water was presented for 10 min, after which a filter paper scented with 271 μmol of a thiazoline-related compound (2-methyl-2-thiazoline; 2MT) or an odor molecule that induces learned fear (anisole) was presented for 20 min. The information of body temperature was recorded every 10 sec using Dataquest A.R.T. software (DataScience international). The value of the core body temperature change was calculated as the difference between the mean core body temperature for 10 min when water was presented and the mean core body temperature for 20 min when each odor molecule was presented, and the change in the core body temperature without odor was set to 0. The mice presented with the odor that induces learned fear were trained to associate the anisole odor with electric shock one day before the measurement, whereby the mice learned to feel learned fear against the smell of anisole.

Results

Figure 4:
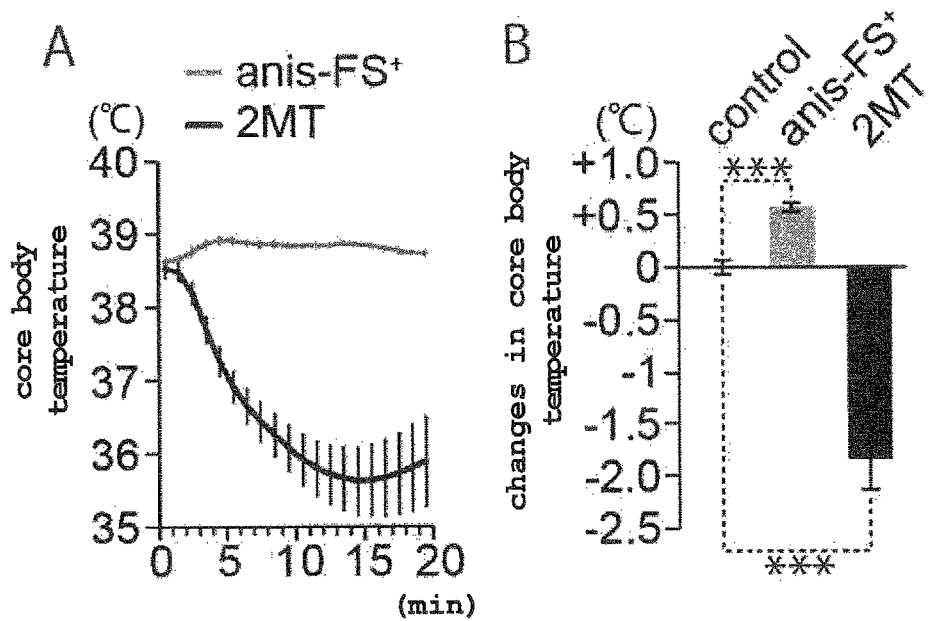
FIG. 4 A: Figure showing time-course changes (mean±standard error) in the core body temperature when 2MT or an odor molecule that induces learned fear (anis-FS$^+$) was smelled. B: Figure showing mean changes in the core body temperature for 20 min when 2MT or an odor molecule that induces learned fear (anis-FS$^+$) was presented.

The results are shown in FIG. 4.

FIG. 4A shows time-course changes (mean±standard error) in the core body temperature when thiazoline-related compound (2MT) or an odor molecule that induces learned fear (anis-FS$^+$) was smelled (n 8).

FIG. 4B shows mean changes in the core body temperature for 20 min when thiazoline-related compound (2MT) or an odor molecule that induces learned fear (anis-FS$^+$) was presented. The graph shows the values of mean±standard error, and Student's t-test was performed on the changes in the body surface temperature without odor (control) and when odor was presented. *** means the presence of a significant difference at p<0.001.

The thiazolin-related compound (2MT) caused a clear decrease in the core body temperature. In contrast, the odor molecule (anis-FS+) that induces learned fear caused a significant increase in the body surface temperature.

Example 5: Heart Rate Decrease Induced by Thiazoline-Related Compound

Experiment Method

An influence of a thiazoline-related compound and an odor molecule that induces learned fear on the heart rate was analyzed. A radio-telemetry device for monitoring biological parameters (manufactured by Physiotel) was surgically implanted in the abdomen of male C57/BL6N mice (about 3 months old). The mice were subjected to the following experiment after about 10 days of recovery period. Each mouse was placed in a test cage and, after acclimation for 10 min, a filter paper dropped with water was presented for 10 min, after which a filter paper scented with 271 μmol of a thiazoline-related compound (2-methyl-2-thiazoline; 2MT) or an odor molecule that induces learned fear (anisole) was presented for 20 min. The information of heart rate was recorded every 10 sec using Dataquest A.R.T. software (DataScience international). The value of the heart rate change was calculated as the difference between the heart rate for 10 min when water was presented and the mean heart rate for 20 min when each odor molecule was presented, and the change in the heart rate without odor was set to 0. The mice presented with the odor that induces learned fear were trained to associate the anisole odor with electric shock one day before the measurement, whereby the mice learned to feel learned fear against the smell of anisole.

Results

Figure 5:
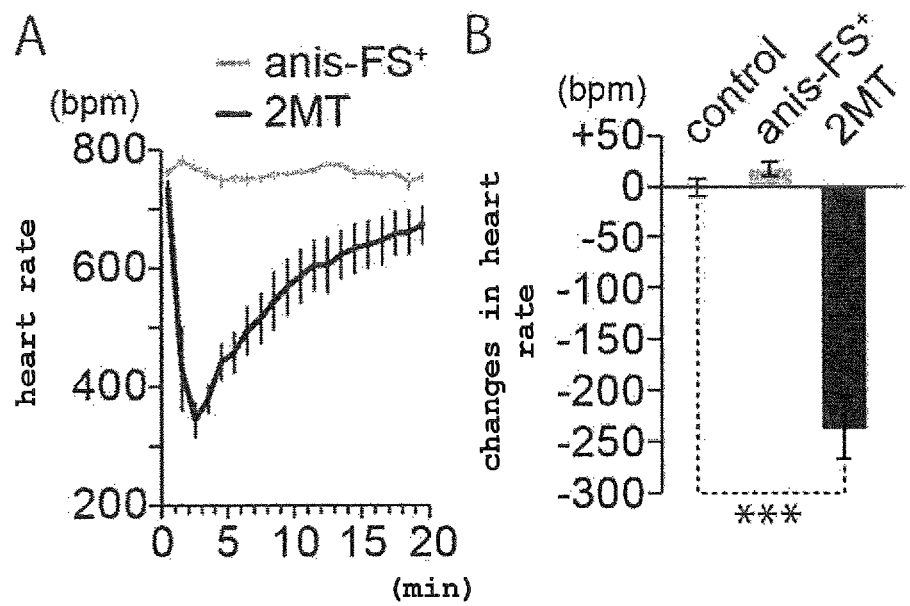
FIG. 5 A: Figure showing time-course changes (mean±standard error) in the heart rate when 2MT or an odor molecule that induces learned fear (anis-FS$^+$) was smelled. B: Figure showing mean changes in the heart rate for 20 min when 2MT or an odor molecule that induces learned fear (anis-FS$^+$) was presented.

The results are shown in FIG. 5.

FIG. 5A shows time-course changes (mean±standard error) in the heart rate when thiazoline-related compound (2MT) or an odor molecule that induces learned fear (anis-FS$^+$) was smelled (n≥8).

FIG. 5B shows mean changes in the heart rate for 20 min when thiazoline-related compound (2MT) or an odor molecule that induces learned fear (anis-FS$^+$) was presented. The graph shows the values of mean±standard error, and Student's t-test was performed on the changes in the body surface temperature without odor (control) and when odor was presented. *** means the presence of a significant difference at p<0.001.

The thiazolin-related compound (2MT) caused a clear decrease in the heart rate such as decrease in the heart rate to half within 3 min and the like. In contrast, the odor molecule (anis-FS+) that induces learned fear did not cause a significant influence on the heart rate.

Example 6: Skin Blood Flow Decrease Induced by Thiazoline-Related Compound

Experiment Method

An influence of a thiazoline-related compound and an odor molecule that induces learned fear on the skin blood flow was analyzed. Male C57/BL6N mice (about 3 months old) were anesthetized with pentobarbital (50 mg/kg, i.p.) about 5 days before the test, and the back hair was depilated with depilatory cream. A mouse restrainer having an observation window was prepared using a 50 ml tube, the mice were trained to enter the restrainer from the day after hair removal, and acclimated by performing this operation until the day before the test. On the day of testing, each mouse was placed in a restrainer, and a laser Doppler probe was attached to the shaved back of the mouse with an adhesive tape. After confirming that the blood flow signal became stable, (1) no odor was presented for 10 min, (2) Eugenol odor was presented for 10 min, (3) thiazoline-related compound (2MT) or an odor that induces learned fear (Anis-FS+) was presented for 20 min, and changes in the blood flow were measured. The odors were presented to the mice by bringing filter papers scented with 271 μmol of odor molecules close to the tip of the nose. The blood flow rate was measured every 10 seconds using a laser Doppler blood flow meter (ADVANCE CO., LTD. ALF21D). The mean skin blood flow without odor (10 min) or with the presentation of a thiazoline-related compound or an odor that induces learned fear (20 min) was calculated, and the mean skin blood flow was shown as a relative value with the mean skin blood flow without odor as 100%.

Results

Figure 6:
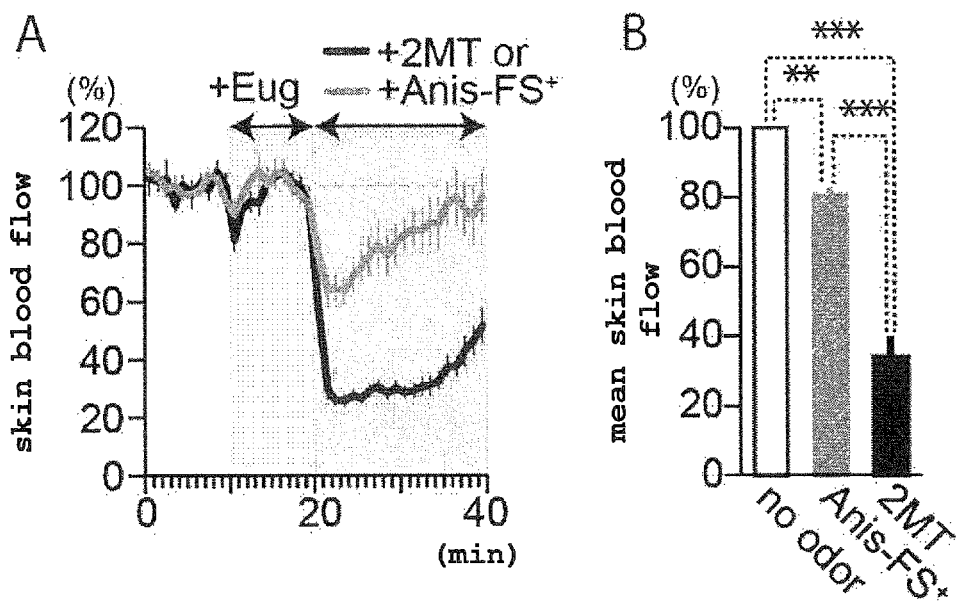
FIG. 6 A: Figure showing time-course changes (mean±standard error) in the blood flow when 2MT or an odor molecule that induces learned fear (Anis-FS$^+$) was smelled. B: Figure showing mean skin blood flow with no odor or when 2MT or an odor molecule that induces learned fear (Anis-FS$^+$) was presented.

The results are shown in FIG. 6.

FIG. 6A shows time-course changes (mean±standard error) in the blood flow when thiazoline-related compound (2MT) or an odor molecule that induces learned fear (anis-FS[+]) was smelled (n≥8).

FIG. 6B is a bar graph showing mean skin blood flow with no odor or when thiazoline-related compound (2MT) or an odor molecule that induces learned fear (Anis-FS[+]) was presented. The graph shows the values of mean±standard error, and Student's t-test was performed on the blood flow without odor and when odor was presented.  means the presence of a significant difference at $p<0.01$, and * at $p<0.001$. The thiazoline-related compound and the odor molecule that induces learned fear both decreased the skin blood flow.

Two possible mechanisms, namely, promotion of heat exchange by increasing skin blood flow and reduction of heat production were considered for the mechanism of inducing a decrease in the body temperature by the thiazoline-related compound. However, the results suggest that the thiazoline-related compound induces a decrease in heat production rather than promoting the heat exchange.

Example 7: Respiratory Rate Decrease Induced by Thiazoline-Related Compound

Experiment Method

An influence of a thiazoline-related compound and an odor molecule that induces learned fear on the respiratory rate was analyzed. The respiratory rate was analyzed using a pulse oximeter (Mouse Oxplus; STARR Life Science). A pulse oximeter was attached to the neck of C57/BL6N male mice (about 3-month-old) from about 1 week before the test and the mice were acclimated by repeating this operation. The mice were anesthetized with pentobarbital (50 mg/kg, i.p.) 2 days before the test, and the neck hair was depilated with depilatory cream. On the day of testing, an oximeter probe was attached to the shaven neck. After confirming that the signal became stable, the no odor baseline was measured for 10 min, changes in the respiratory rate when the thiazoline-related compound (2MT) or neutral odor (Eugenol; Eug) was presented was measured for 20 min (each n=6). The odors were presented by placing filter papers scented with 271 μmol of odor in the test cage. The oximeter signal was obtained at 1 Hz. The mean respiratory rate shows mean respiratory rate after no odor for 10 min or 20 min after presenting odor.

Results

Figure 7:
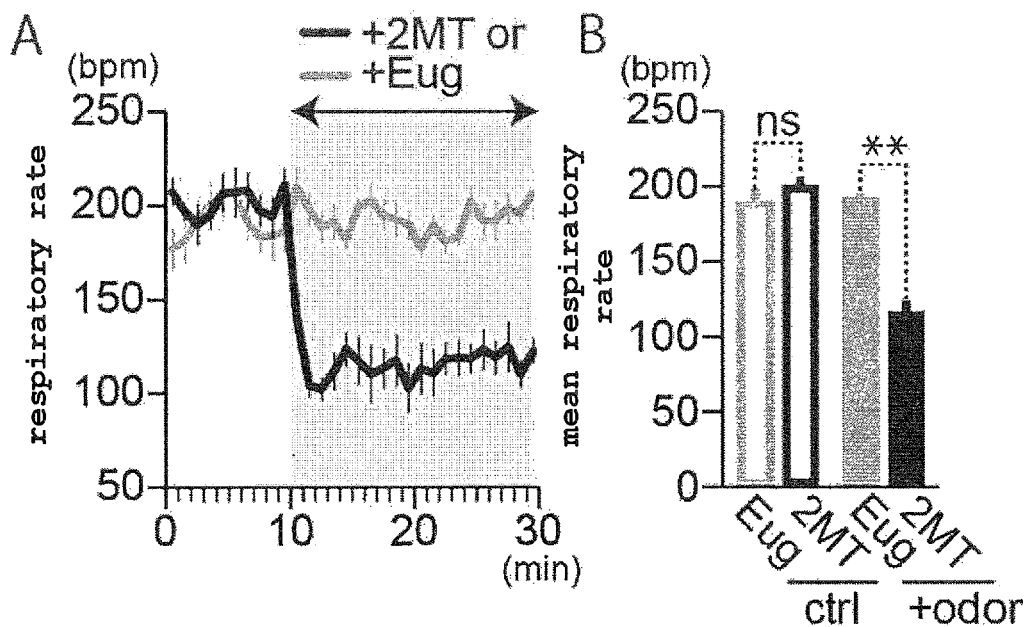
FIG. 7 A: Figure showing time-course changes (mean±standard error) in the respiratory rate when 2MT or a spice odor (Eug) was smelled. B: Figure showing mean respiratory rate with no odor or when 2MT or a spice odor (Eug) was presented.

The results are shown in FIG. 7.

FIG. 7A shows time-course changes (mean±standard error) in the respiratory rate when thiazoline-related compound (2MT) or a spice odor (Eug) was smelled (n=6).

FIG. 7B is a bar graph showing mean respiratory rate of the no odor baseline (ctrl) and mean respiratory rate when odor (Eug or 2MT) was presented in the group presented with spice odor (Eug) and the group presented with thiazoline-related compound (2MT). The graph shows the values of mean±standard error, and the Student's t-test was performed on the respiratory rate of the group presented with 2MT and the group presented with Eug. ** means the presence of a significant difference at $p<0.01$, and ns means no significant difference at $p>0.05$.

It was clarified that the thiazoline-related compound reduced the respiratory rate by about half. Decreased body temperature and reduced metabolism are observed in animals during hibernation, and it is well known that hibernating animals have reduced respiratory rates. It was clarified that the thiazoline-related compound also causes a decrease in respiratory rate as observed in hibernation.

Example 8: Oxygen Consumption Decrease Induced by Thiazoline-Related Compound

Experiment Method

An influence of a thiazoline-related compound on the oxygen consumption was analyzed. The oxygen consumption was analyzed using an energy metabolism measurement device for small animals (ARCO-2000; ARCO SYSTEM). About 3-month-old C57/BL6N male mice were each placed in a measuring chamber and, after acclimation for about 2 hr, a thiazoline-related compound (2MT) was presented. The odors were presented by placing filter papers scented with 100 μl (104 mmol) of odor molecules in the measuring chamber. As a control, an experiment in which a filter paper dropped with saline was presented to the mice was also performed. The oxygen consumption was measured every one min. Mean oxygen consumption was calculated as the mean of 10 min before presenting odor and 20 min after presenting odor.

Results

Figure 8:
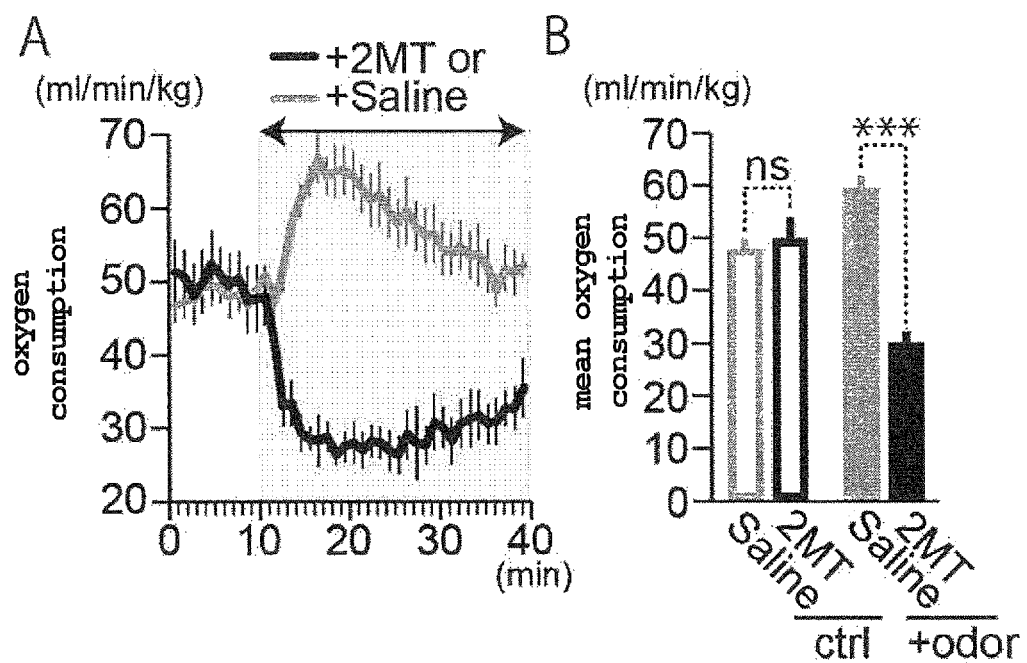
FIG. 8 A: Figure showing time-course changes (mean±standard error) in the oxygen consumption per body weight of mouse when 2MT was presented or with no odor (Saline). B: Figure showing mean oxygen consumption per body weight of mouse when 2MT was presented or with no odor.

The results are shown in FIG. 8.

FIG. 8A shows time-course changes (mean±standard error) in the oxygen consumption per body weight of mouse when the thiazoline-related compound (2MT) was presented or with no odor (Saline) (n=8).

FIG. 8B is a bar graph showing mean oxygen consumption per body weight of mouse when the thiazoline-related compound (2MT) was presented or with no odor (Saline). The graph shows the values of mean±standard error, and the Student's t-test was performed on the oxygen consumption when 2MT or Saline was presented. *** means the presence of a significant difference at $p<0.001$, and ns means no significant difference at $p>0.05$.

Under the control (saline) condition, the oxygen consumption was increased by presenting a new substance (filter paper). In contrast, when the thiazoline-related compound (2MT) was presented, the oxygen consumption was decreased remarkably. Oxygen consumption is known to decrease as the metabolism decreases in hibernating animals. It was shown that similar changes are induced by the thiazoline-related compound.

Example 9: Hypoxia Resistance Induced by Thiazoline-Related Compound

Experiment Method

About 3-month-old C57/BL6N male mice were each placed in a highly sealed breeding cage, and a filter paper scented with 100 μl (104 mmol) of the thiazoline-related compound (2MT) was placed in the breeding cage, and the odor was presented for 50 min. After the odor was presented, the mice were placed in a tight box in which the oxygen concentration was adjusted to 4%, and the survival time of the mice was measured up to 30 min at maximum. As a control, the survival time of mice presented with a filter paper dropped with water was also measured (no odor). Furthermore, changes in the core body temperature when the odor was presented under the same conditions as in this Example were measured by the same experimental method as in Example 4.

Results

Figure 9:
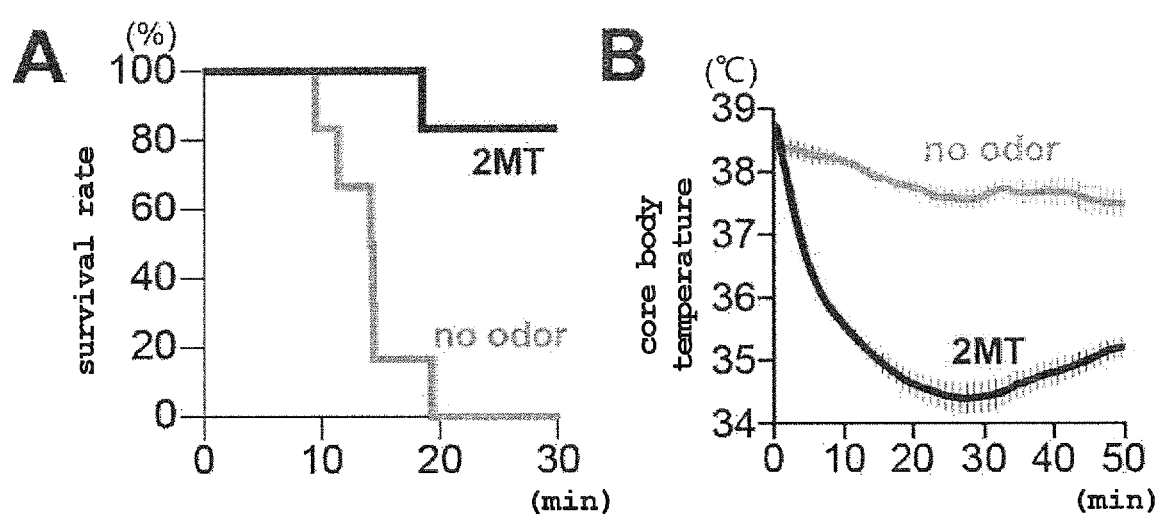
FIG. 9 A: Figure showing the survival time of mouse in 4% oxygen when 2MT was presented or with no odor by the Kaplan-Meier curve. B: Figure showing time-course changes (mean±standard error) in the core body temperature when odor was presented under the same conditions as in the example of A.

The results are shown in FIG. 9.

FIG. 9A shows the survival time of mouse in 4% oxygen when thiazoline-related compound (2MT) was presented or with no odor by the Kaplan-Meier curve (each n=6).

FIG. 9B shows time-course changes (mean±standard error) in the core body temperature when odor was presented under the same conditions as in the example of FIG. 9A (2MT, n=8; no odor, n=6).

Under the control condition without odor, all individuals died within 20 min in 4% oxygen, whereas many individuals survived even after 30 min in the condition where the thiazoline-related compound (2MT) was presented. Even under the odor presentation conditions adopted in this example, a remarkable decrease in the core body temperature was observed. It was shown that the thiazoline-related compound causes hypoxia resistance.

Example 10: Hypoxia Resistance Induced by Various Heterocyclic Compounds

Experiment Method

Influence of intraperitoneal administration of various kinds of heterocyclic compounds on the survival time of mouse under hypoxic environment was analyzed. The odor molecule was administered by a method of intraperitoneally injecting 200 μl (about 80 mg/kg, i.p.) of a solution diluted 100 times with saline and, 30 min later, the mice were placed in a tight box with adjusted oxygen concentration of 4%, and the survival time of the mouse was measured for 30 min at maximum. As a control, the survival time of the mice intraperitoneally injected with saline (control) was measured.

Results

Figure 10A:
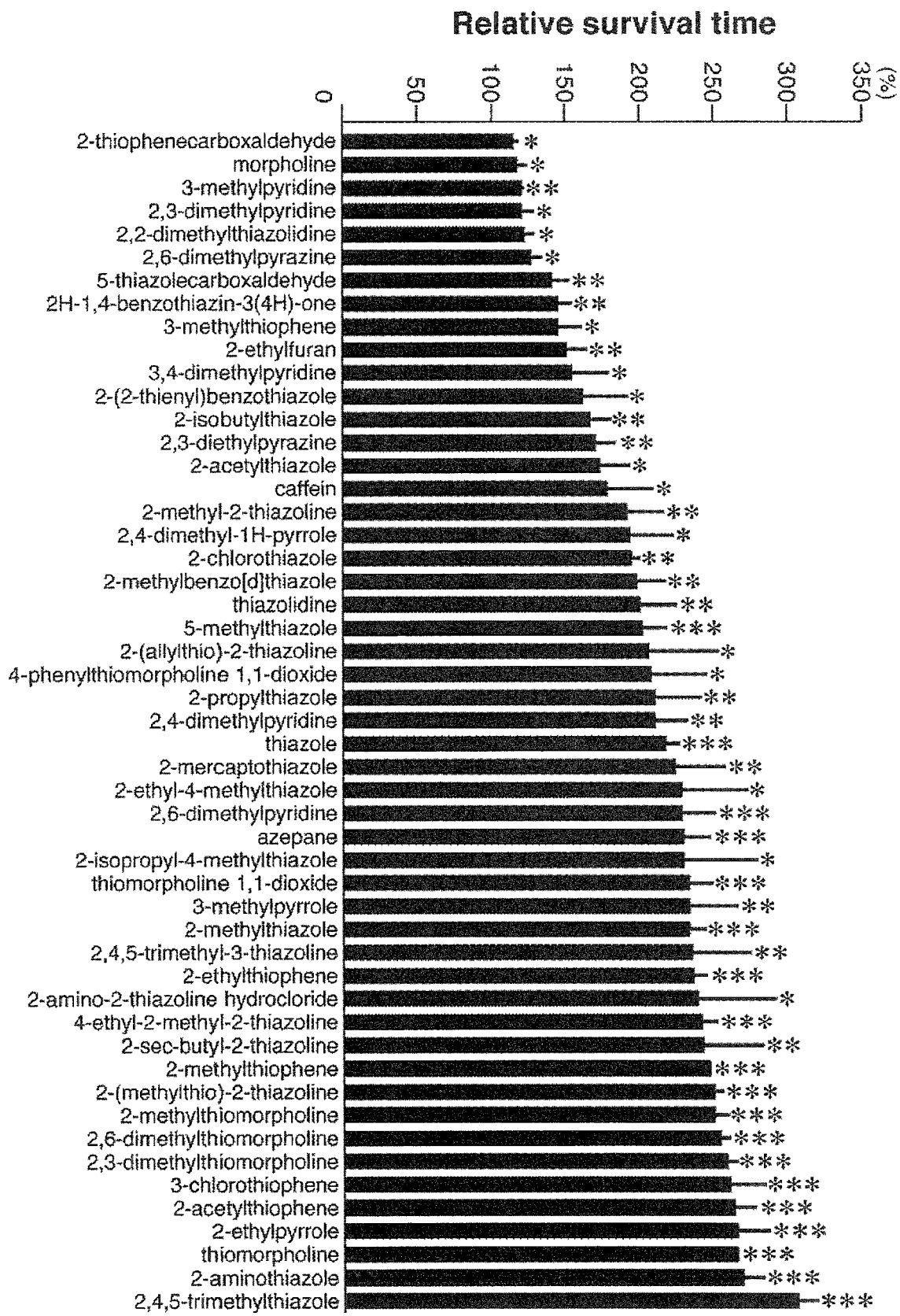
FIG. 10A shows the survival time (mean±standard error) of mouse in 4% oxygen when each heterocyclic compound was intraperitoneally injected.

The results are shown in FIG. 10A.

FIG. 10A is a bar graph showing the survival time (mean±standard error) of mouse in 4% oxygen when each heterocyclic compound was intraperitoneally injected. The survival time was shown as a relative value (%) with the mean survival time of the control intraperitoneally injected with saline as 100% (n=4). Student's t-test was performed on the survival time between the control group and each compound administration group. * means the presence of a significant difference at p<0.05,  at p<0.01, and * at p<0.001.

Figure 10B:
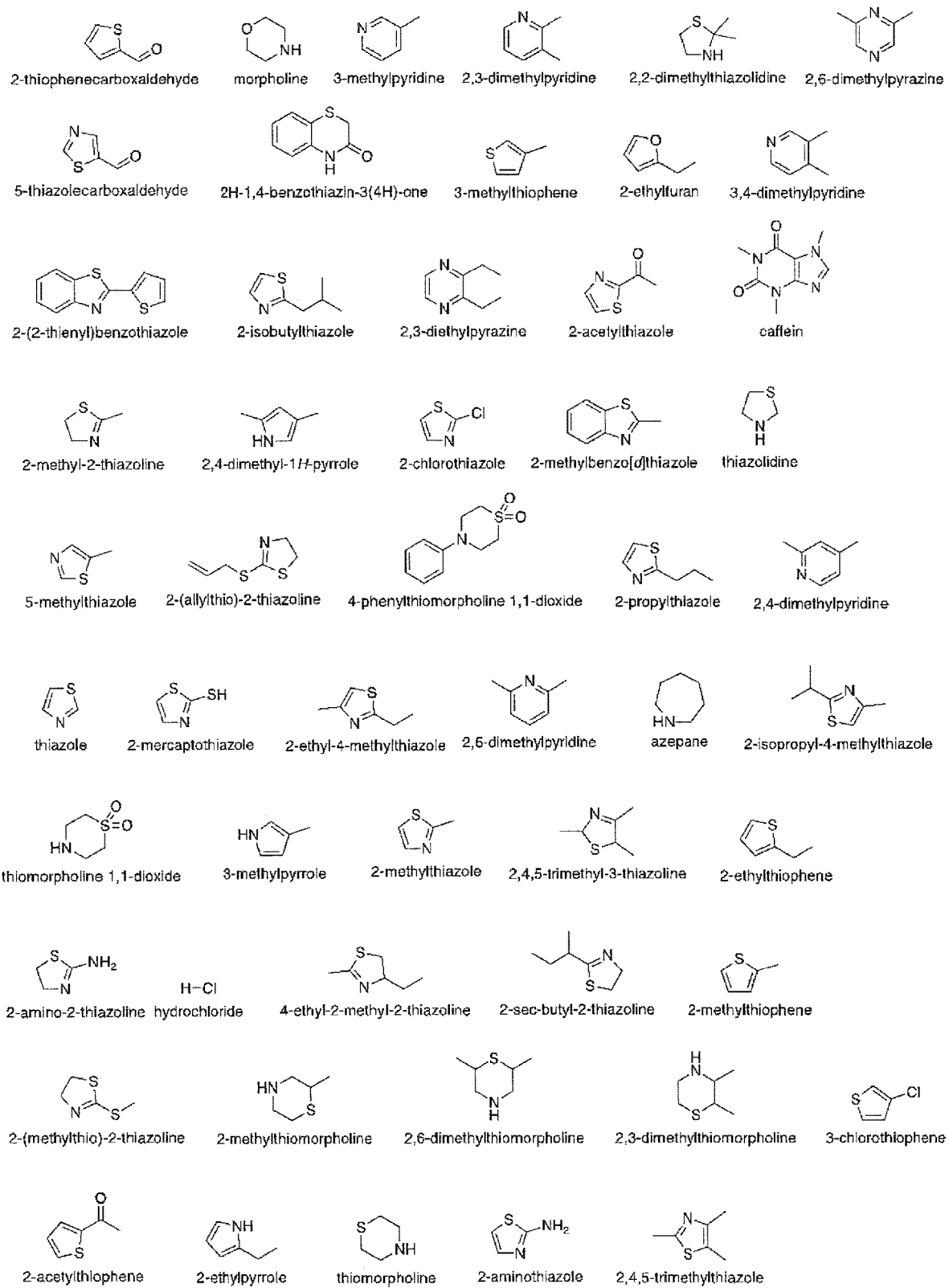
FIG. 10B shows the structural formulas of the compounds used in Example 10 in the order in the graph of FIG. 10A.

FIG. 10B shows the structural formulas of the compounds used in Example 10 in the order in the graph.

It was shown that various kinds of heterocyclic compounds produce hypoxia resistance.

Example 11: Hypoxia Resistance Induced by Isothiocyanate Compound

Experiment Method

By a method similar to that in Example 10, influence of intraperitoneal administration of various isothiocyanate compounds (about 80 mg/kg, i.p.) on the survival time of mouse under hypoxic environment was analyzed.

Results

Figure 11A:
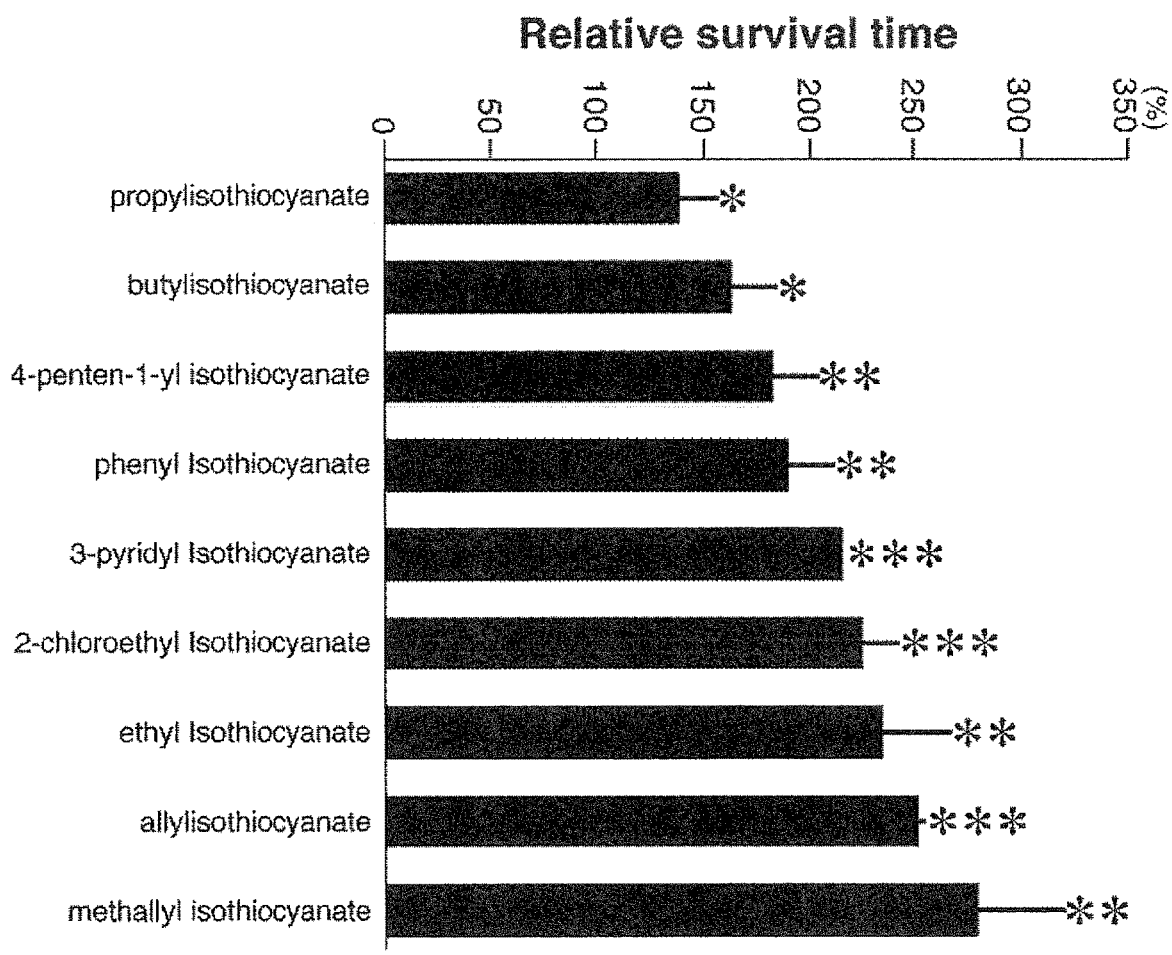
FIG. 11A shows the survival time (mean±standard error) of mouse in 4% oxygen when each isothiocyanate compound was intraperitoneally injected.

The results are shown in FIG. 11A.

FIG. 11A is a bar graph showing the survival time (mean±standard error) of mouse in 4% oxygen when each compound was intraperitoneally injected. The survival time was shown as a relative value (%) with the mean survival time of the control intraperitoneally injected with saline as 100% (n=4). Student's t-test was performed on the survival time between the control group and the groups administered with test compounds. * means the presence of a significant difference at p<0.05,  at p<0.01, and * at p<0.001.

Figure 11B:
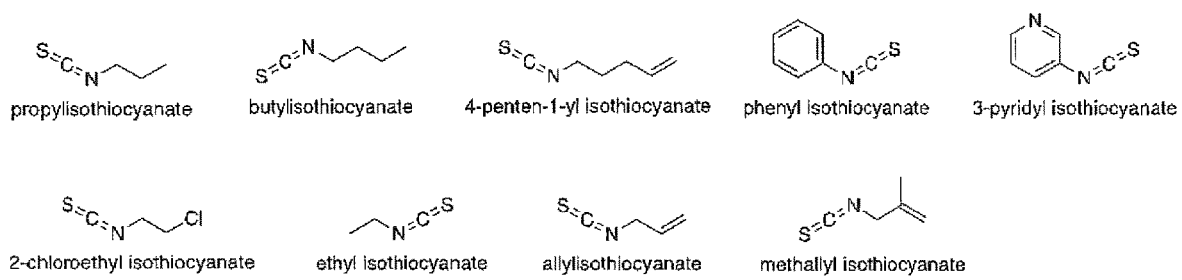
FIG. 11B shows the structural formulas of the compounds used in Example 11 in the order in the graph of FIG. 11A.

FIG. 11B shows the structural formulas of the compounds used in Example 11 in the order in the graph.

It was shown that various isothiocyanate compounds produce hypoxia resistance.

Example 12: Hypoxia Resistance Induced by Intraperitoneal Administration of Thiomorpholine Experiment Method About 3-month-old C57/BL6N male mice were intraperitoneally injected with 200 μl (about 80 mg/kg, i.p.) of a thiomorpholine solution diluted 100 times with saline and, 30 min later, the mice were placed in a tight box with adjusted oxygen concentration of 4%, and the survival time of the mouse was measured. As a control, the survival time of the mice intraperitoneally injected with saline was measured.

Results

Figure 12:
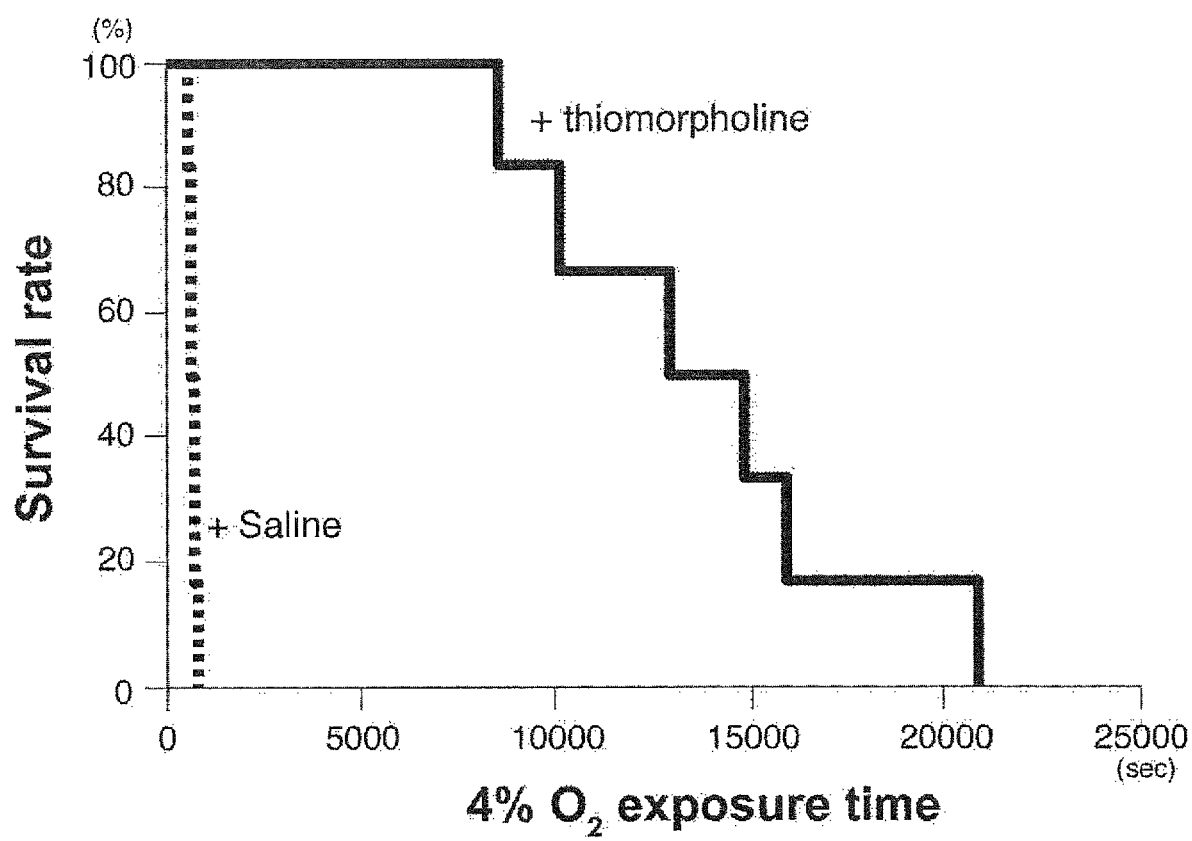
FIG. 12 shows the survival time of mouse in 4% oxygen when thiomorpholine and saline were administered by the Kaplan-Meier curve.

The results are shown in FIG. 12.

FIG. 12 shows the survival time of mouse in 4% oxygen when thiomorpholine and saline were administered by the Kaplan-Meier curve (n=6).

It was shown that thiomorpholine produces hypoxia resistance.

Example 13: Influence on Survival Time Under 4% Oxygen Conditions by Intraperitoneal Administration of NaHS Experiment Method About 3-month-old C57/BL6N male mice were intraperitoneally injected with 200 μl of a NaHS solution and the mice were placed in a tight box with adjusted oxygen concentration of 4%, and the survival time of the mouse was measured for 30 min at maximum. NaHS solutions having 4 kinds of concentrations of 0.1%, 0.125%, 0.05%, 0.0125% were used. Among these, when the 0.1% solution was intraperitoneally injected, the mice died within several minutes. Thus, the survival time was measured at the remaining three concentrations. As a control, the survival time of the mice intraperitoneally injected with saline or 2-methylthiophene (1% solution) in 4% oxygen was measured.

Results

Figure 13:
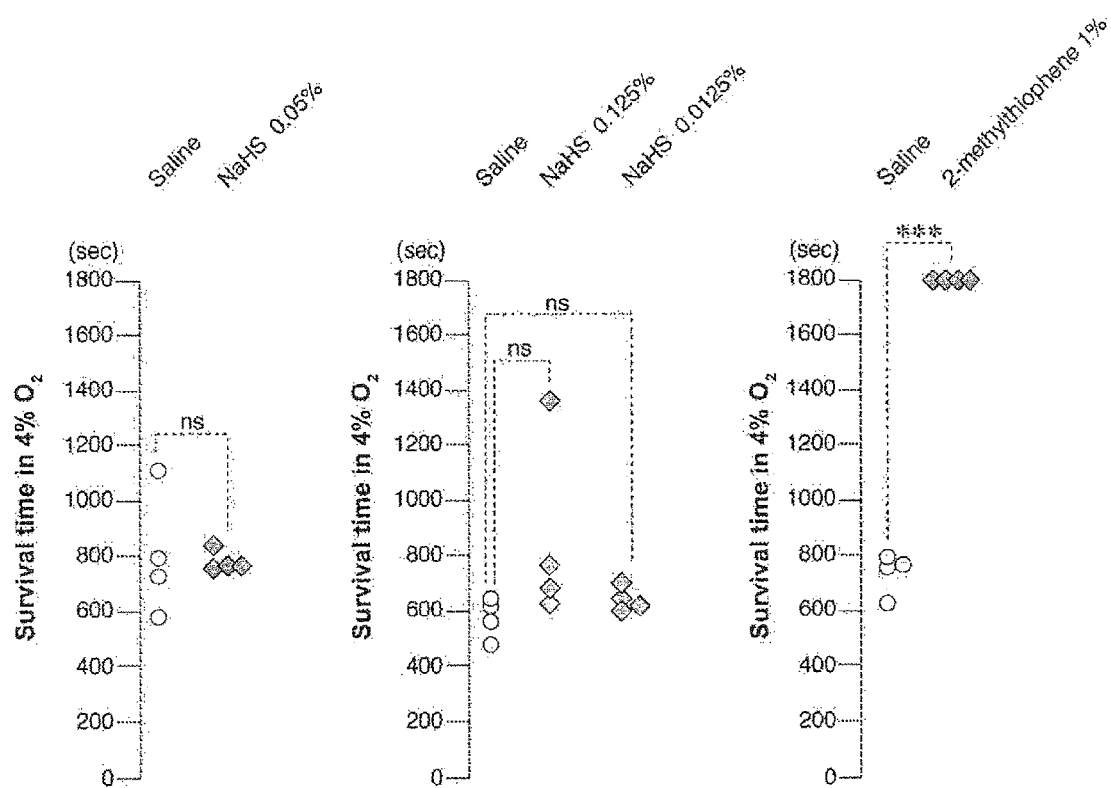
FIG. 13 is a Figure in which the survival time of mouse intraperitoneally injected with each solution shown in the Figure is plotted for each individual.

The results are shown in FIG. 13.

In FIG. 13, the survival time of mice intraperitoneally injected with each solution shown in FIG. 13 is plotted for each individual. Student's t-test was performed on the survival time between the two groups marked with a dotted line. *** means the presence of a significant difference at p<0.001, and ns means no significant difference at p>0.05.

NaHS, which is a donor of $H_2S$, has been reported to have protective effects in ischemia-reperfusion injury (Yu et al., Cell Physiol Biochem 36: 1539-1551, 2015). However, at high concentrations of NaHS, the mice died promptly after injection, and at low concentrations, hypoxia resistance was not observed. In contrast, the mice administered with 2-methylthiophene, which is one of the thiazoline-related compounds, showed survival in 4% oxygen during the observation time of 30 min in all individuals.

Example 14: Ischemia-Reperfusion Injury Reducing Effect by Thiazoline-Related Compound Experiment Method Skin ischemia-reperfusion injury model mouse was generated as follows according to the method of Uchiyama et al. (Uchiyama et al., Sci Rep 5: 9072, 2015). The back hair of C57/BL6N male mice (about 3-month-old) was shaved in the same manner as in Example 1, 2-3 days before the test. On the day of the test, the mice were each placed in a highly sealed cage, and a filter paper scented with 100 μl (104 mmol) of the thiazoline-related compound (2MT) was placed in the breeding cage, and the odor was presented for 30 min. As a control, a filter paper dropped with water was presented for 30 min (no odor). After 30 min, the mouse was taken out from the cage, the dorsal skin was pinched between two circular magnets and the mouse was returned to the highly sealed cage. Furthermore, a filter paper scented with 100 μl (104 mmol) of 2 MT or water was placed in the highly sealed cage, and the mouse was left for 12 hr. After 12 hr, the mouse was taken out from the highly sealed cage, the magnets were removed, and the mouse was transferred to a normal breeding cage with no odor. The condition of the skin on the back, which was pinched between magnets, was recorded by taking photographs every day. Based on the obtained images, the wound area was quantified with image analysis software (Photoshop, Adobe). Furthermore, changes in the core body temperature when the odor was presented under the same conditions as in this Example were measured by the same experimental method as in Example 2.

Results

Figure 14:
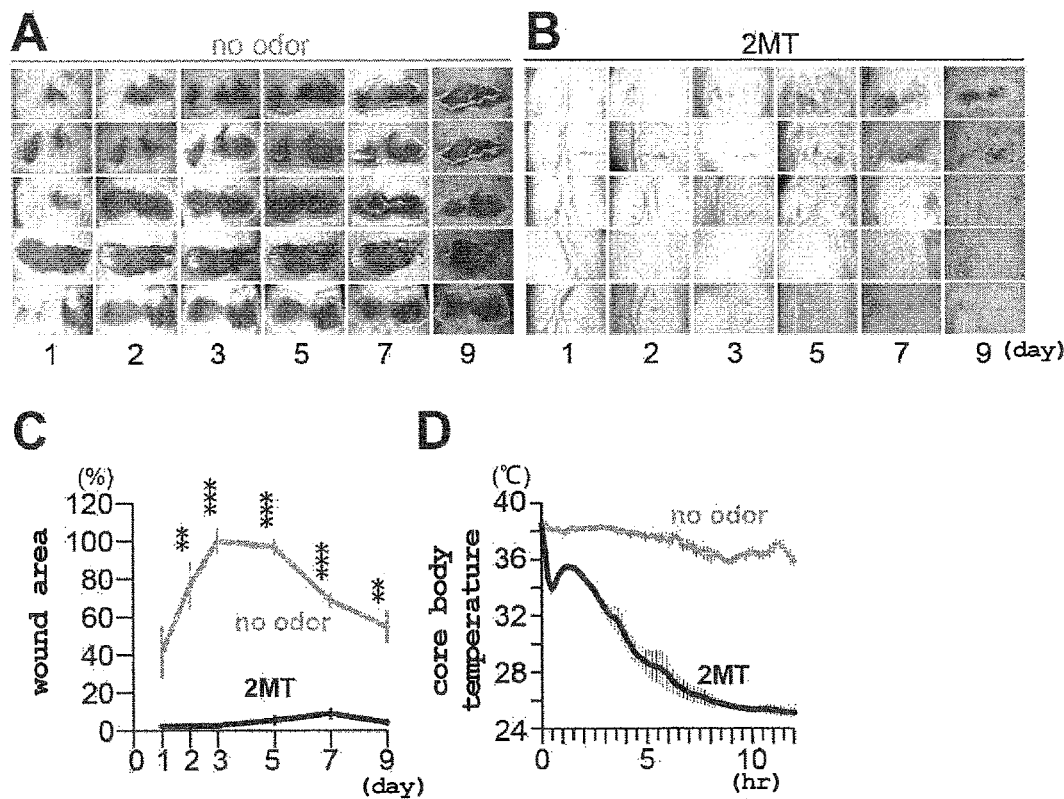
FIG. 14 A: Photographs showing the results of daily observation of changes in the wound site under no odor conditions for each individual. B: Photographs showing the results of daily observation of changes in the wound site under conditions with presentation of 2MT. C: Figure showing quantification of the wound area observed in A and B. D: Figure showing time-course changes (mean±standard error) in the core body temperature when odor was presented under the same conditions as in the examples of A-C.

The results are shown in FIG. 14.

FIG. 14A shows the results of daily observation of changes in the wound site under no odor conditions for each individual (n=5).

FIG. 14B shows the results of daily observation of changes in the wound site under conditions with presentation of 2MT (n=5).

FIG. 14C shows quantification of the wound area observed in A and B. The graph shows time-course changes in the wound area (mean±standard error) as relative values with the mean of the wound area under the condition without odor 3 days later being 100%. Student's t-test was performed on the wound area with 2MT or with no odor observed on the same day.  means a significant difference at $p<0.01$, and * means a significant difference at $p<0.001$.

FIG. 14D shows time-course changes (mean±standard error) in the core body temperature when odor was presented under the same conditions as in the example of A-C (each n=6).

In the control with no odor, pressure ulcer was formed by pinching the skin between magnets for 12 hr, whereas the formation of pressure ulcer significantly decreased under the condition where 2MT was smelled. Even under the odor presentation conditions adopted in this example, a remarkable decrease in the core body temperature was observed. Pressure ulcer is caused by an ischemic state due to prolonged pressure. It was shown that the thiazoline-related compound has the effect of reducing or preventing ischemia-reperfusion injury.

Example 15: Changes in Body Surface Temperature of Trpa1 Knockout Mouse by Thiazoline-Related Compound Experiment Method Using about 3-month-old male Trpa1 knockout and littermate hetero mice, changes in the body surface temperature induced by the thiazoline-related compound (2MT) was analyzed by a method similar to that in Example 1. The changes in the body surface temperature were calculated as a difference obtained by subtracting the mean body surface temperature during acclimation with no odor from the mean body surface temperature for 20 min with presentation of 2MT.

Results

Figure 15:
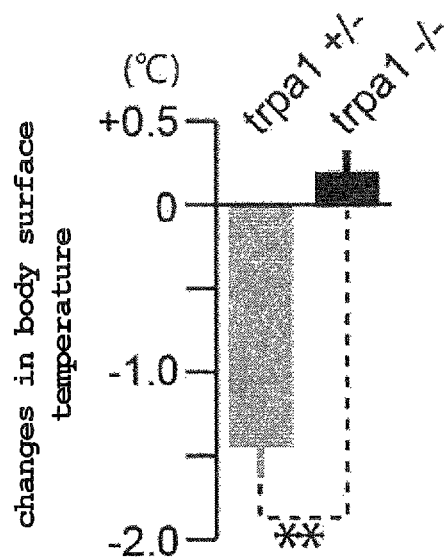
FIG. 15 shows mean changes in the body surface temperature when 2MT was presented to the control mouse (trpa1$^{+/-}$; n=5) and Trpa1 knockout mouse (trpa1$^{-/-}$; n=8).

The results are shown in FIG. 15.

FIG. 15 shows mean changes in the body surface temperature when thiazoline-related compound (2MT) was presented to the control mice (trpa1$^{+/-}$; n=5) and Trpa1 knockout mice (trpa1$^{-/-}$; n=8). Student's t-test was performed on the changes in the body surface temperature between the control mice and the knockout mice. ** means a significant difference at $p<0.01$.

In the Trpa1 knockout mice, a decrease in the body surface temperature induced by the thiazoline-related compound (2MT) was not observed. It was suggested that the decrease in the body surface temperature by 2MT is induced via Trpa1.

Example 16: Changes in Core Body Temperature of Trpa1 Knockout Mouse by Thiazoline-Related Compound Experiment Method Using about 3-month-old male Trpa1 knockout and littermate hetero mice, changes in the core body temperature induced by the thiazoline-related compound (2MT) was analyzed by a method similar to that in Example 2. The changes in the core body temperature were calculated as a difference obtained by subtracting the mean core body temperature during acclimation with no odor from the mean core body temperature for 20 min with presentation of 2MT.

Results

Figure 16:
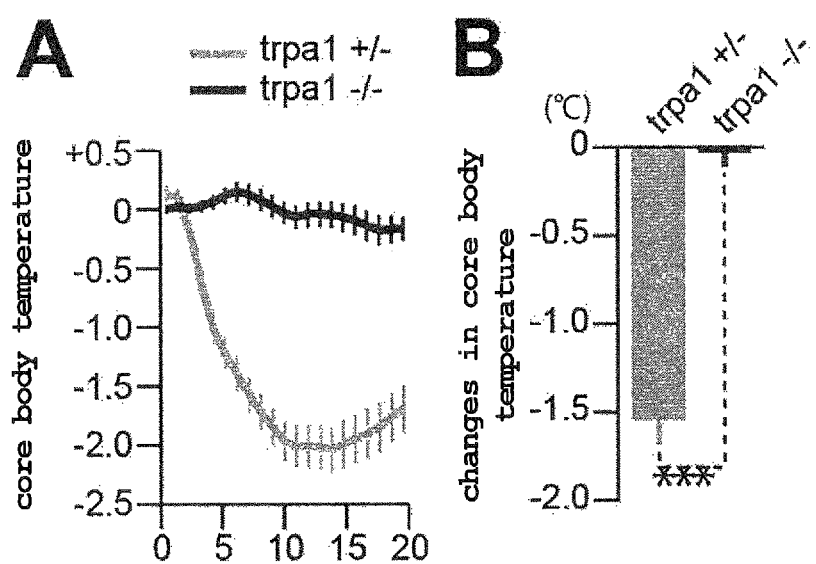
FIG. 16 A: Figure showing time-course changes in the core body temperature when 2MT was presented to the control mouse (trpa1$^{+/-}$; n=7) and Trpa1 knockout mouse (trpa1$^{-/-}$; n=7). B: Figure showing mean changes in the core body temperature when 2MT was presented to the control mouse (trpa1$^{+/-}$) and Trpa1 knockout mouse (trpa1$^{-/-}$).

The results are shown in FIG. 16.

FIG. 16A shows time-course changes in the core body temperature when 2MT was presented to the control mice (trpa1$^{+/-}$; n=7) and Trpa1 knockout mice (trpa1$^{-/-}$; n=7).

FIG. 16B shows changes in the core body temperature when 2MT was presented to the control mice (trpa1$^{+/-}$) and Trpa1 knockout mice (trpa1$^{-/-}$). Student's t-test was performed on the changes in the core body temperature between the control mice and the knockout mice. *** means a significant difference at $p<0.001$.

In the Trpa1 knockout mice, a decrease in the core body temperature induced by the thiazoline-related compound (2MT) was not observed. It was suggested that the decrease in the core body temperature by 2MT is induced via Trpa1.

Example 17: Hypoxia Resistance of Trpa1 Knockout Mouse Induced by Thiazoline-Related Compound Experiment Method The thiazoline-related compound (2MT) was presented for 10 min to about 3-month-old male Trpa1 knockout and littermate hetero mice. Thereafter, the mice were placed in a tight box in which the oxygen concentration was adjusted to 4%, and the survival time of the mice was measured up to 30 min at maximum. The odor was presented by placing a filter paper scented with 271 μmol of 2MT in the breeding cage. As a control, an experiment presenting a filter paper dropped with saline was also performed (no odor).

Results

Figure 17:
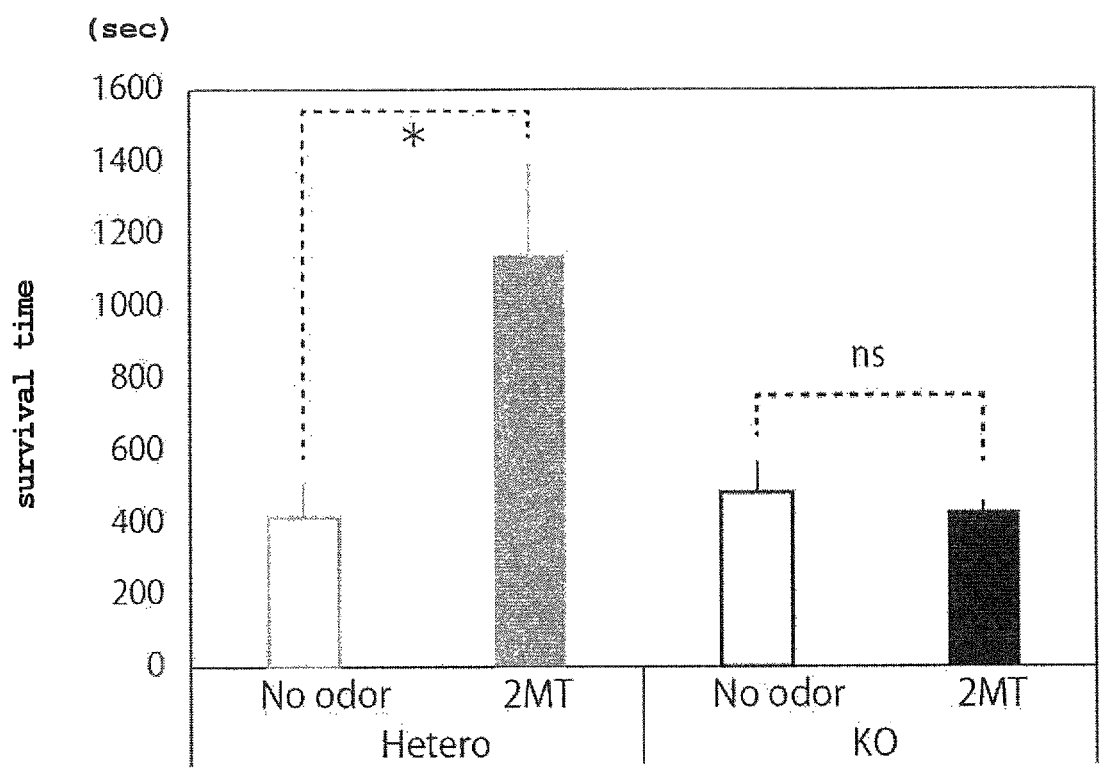
FIG. 17 shows mean survival time in 4% oxygen when saline or 2MT was presented to the control mouse (Hetero) and Trpa1 knockout mouse (KO).

The results are shown in FIG. 17.

FIG. 17 shows mean survival time in 4% oxygen when saline or 2MT was presented to the control mice (Hetero) and Trpa1 knockout mice (KO) (n=6 for no odor of hetero, n=7 for others). Student's t-test was performed on the survival time between presentation of saline and 2MT in each genotype. * means the presence of a significant difference at p<0.05, and ns means no significant difference at p>0.05.

Different from the control mice, the survival time in 4% oxygen did not increase significantly in the Trpa1 knockout mice even when the thiazoline-related compound (2MT) was presented. It was suggested that the hypoxia resistance is induced by the thiazoline-related compound via Trpa1.

Example 18: Blood TNF-α Suppressive Effect by Various Heterocyclic Compounds and Isothiocyanate Compounds in Sepsis Model Experiment Method Lipopolysaccharide (LPS) (0.6 mg/kg) was intraperitoneally administered to male Balb/c mice (about 2-3 months old) to generate a sepsis model. Immediately after the LPS administration, 200 μl (about 80 mg/kg) of a solution prepared by diluting various heterocyclic compounds and isothiocyanate compounds 100 times with saline was intraperitoneally administered. Blood samples were collected 60 min after LPS and compound administration, EDTA plasma was prepared, and the blood level of inflammatory cytokine TNF-α was measured by the ELISA method.

Results

Figure 18:
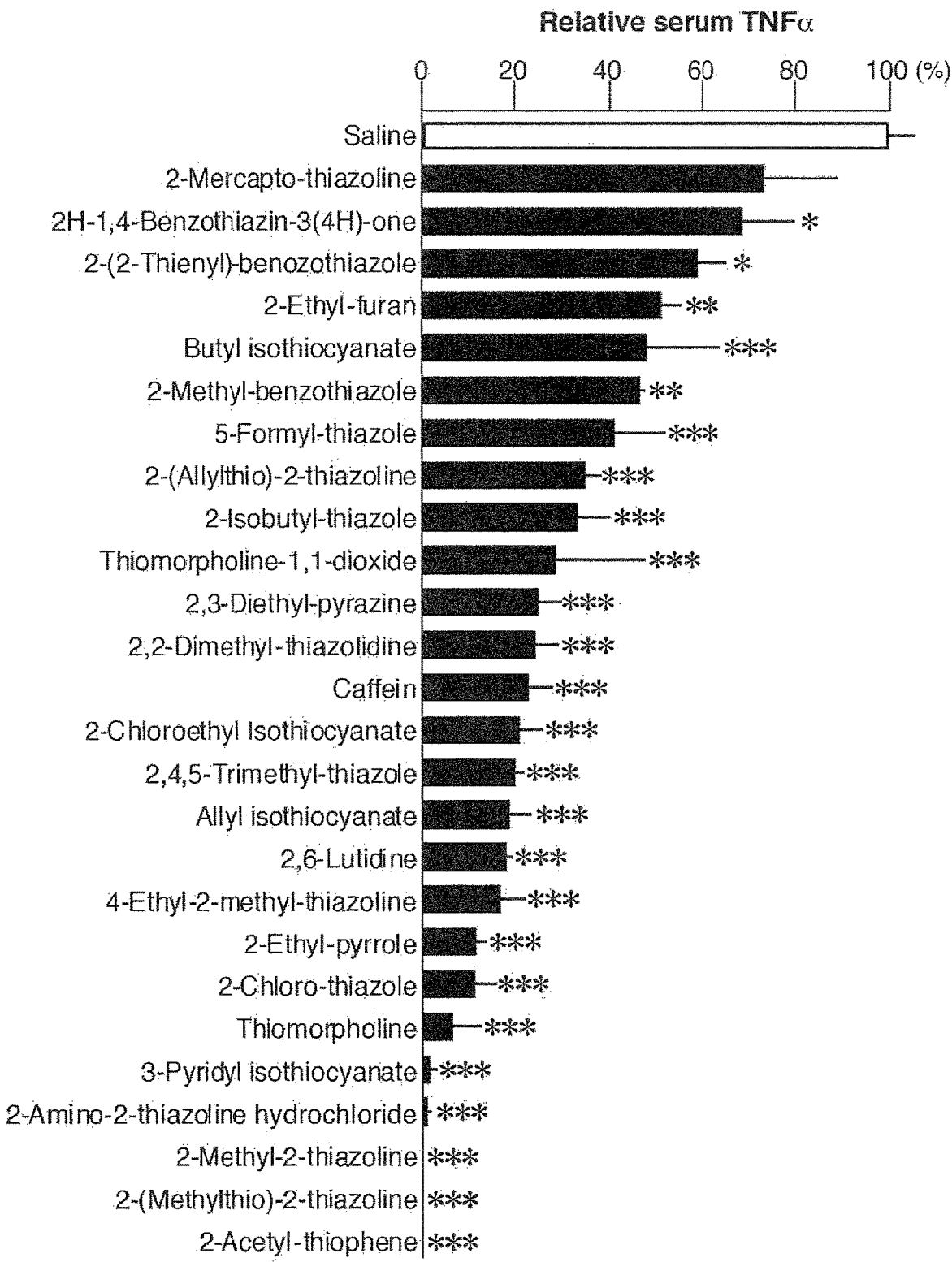
FIG. 18 shows the amount of TNF-α in blood (mean±standard error) when each heterocyclic compound or isothiocyanate compound was intraperitoneally injected to a sepsis model mouse.

The results are shown in FIG. 18. In FIG. 18, "4-Ethyl-2-methyl-thiazoline" means 4-ethyl-2-methyl-2-thiazoline.

The blood TNF-α level (mean±standard error) when each compound was administered is shown in a bar graph. The amount of TNF-α is shown as a relative value (%) with the mean TNF-α amount when only LPS was administered and the compound was not administered (saline) as 100% (n≥4). Student's t-test was performed for the TNF-α amount between the control group (saline) and each compound administration group. * means a significant difference at p<0.5,  means a significant difference at p<0.01, and * means a significant difference at p<0.001. The blood concentration of the inflammatory cytokine TNF-α was decreased by administration of various kinds of heterocyclic compounds and isothiocyanate compounds. Thus, it was shown that these compounds have an anti-inflammatory effect in sepsis model animals.

Example 19: Effect of Thiazoline-Related Compound Against Production of Inflammatory Cytokine and Anti-Inflammatory Cytokine in Sepsis Model Experiment Method A sepsis model mouse was prepared by the same method as in Example 18. Immediately after the LPS administration, 200 μl (about 80 mg/kg) of a thiazoline-related compound (2MT) solution prepared by diluting 100 times with saline was intraperitoneally administered. Blood samples were collected 1 hr and 4 hr after administration of LPS and thiazoline-related compound (2MT), EDTA plasma was prepared, and the blood levels of inflammatory cytokine Interleukin-1β (IL-1β), and anti-inflammatory cytokine Interleukin-10 (IL-10) were measured by the ELISA method.

Results

Figure 19:
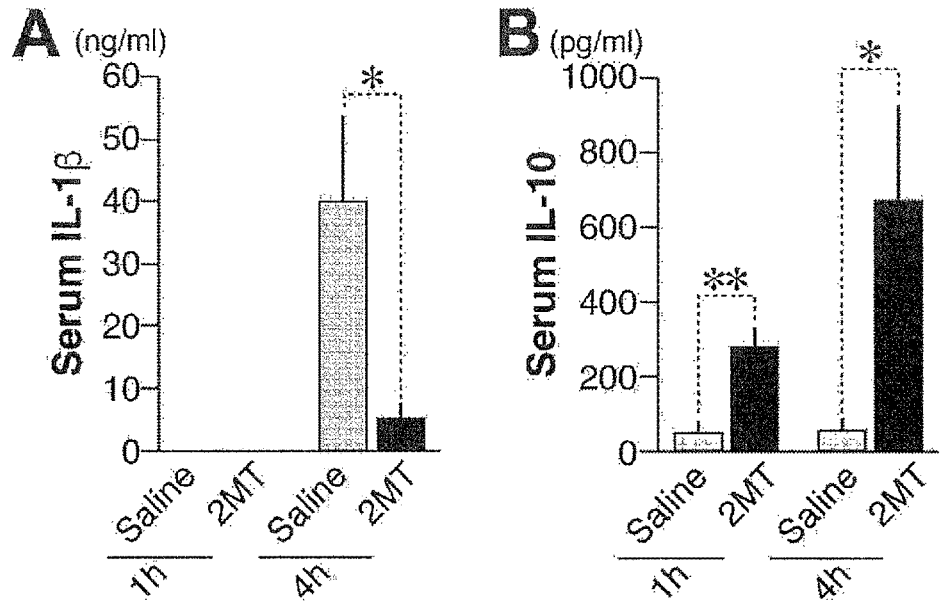
FIG. 19 A: Figure showing the amount of IL-1β in blood (mean±standard error) when 2MT was intraperitoneally injected to a sepsis model mouse. B: Figure showing the amount of IL-10 in blood (mean±standard error) when 2MT was intraperitoneally injected to a sepsis model mouse.

The results are shown in FIG. 19.

The IL-1β amount (FIG. 19A), and IL-10 amount (FIG. 19B) (all mean±standard error) when the thiazoline-related compound (2MT) was administered and when saline, as a control, was administered are shown in a bar graph (n=6). Student's t-test was performed between the control group (saline) and the group administered with thiazoline-related compound (2MT) under respective conditions. * means a significant difference at p<0.05, and ** means a significant difference at p<0.01. Administration of the thiazoline-related compound decreased the blood concentration of inflammatory cytokine IL-1β, and conversely increased the blood concentration of anti-inflammatory cytokine IL-10. Thus, it was shown that the thiazoline-related compound has an anti-inflammatory effect in sepsis model animals.

Example 20: Suppressive Effect of Inflammatory Mediator HMGB1 by Thiazoline-Related Compound in Sepsis Model Experiment Method A sepsis model mouse was prepared by the same method as in Example 18. Immediately after the LPS administration, 200 μl (about 80 mg/kg) of a thiazoline-related compound (2MT) solution prepared by diluting 100 times with saline was intraperitoneally administered. Blood samples were collected 16 hr after administration of LPS and thiazoline-related compound (2MT), EDTA plasma was prepared, and the blood level of inflammatory mediator High Mobility Group Box 1 (HMGB1) was measured by the ELISA method.

Results

Figure 20:
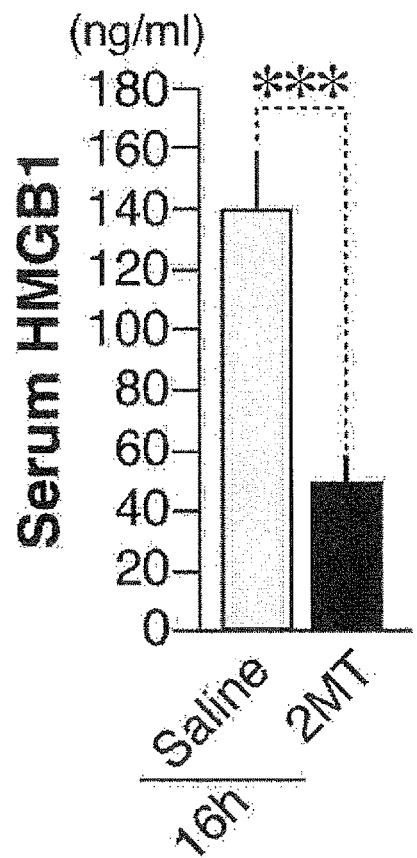
FIG. 20 shows the amount of HMGB1 in blood (mean±standard error) when 2MT was intraperitoneally injected to a sepsis model mouse.

The results are shown in FIG. 20.

The blood HMGB1 amounts (mean±standard error) when the thiazoline-related compound (2MT) was administered and when saline, as a control, was administered are shown in a bar graph (n=6). Student's t-test was performed between the control group (saline) and the group administered with thiazoline-related compound (2MT). *** means a significant difference at p<0.001. Administration of the thiazoline-related compound decreased the blood concentration of inflammatory mediator HMGB1. Thus, it was shown that the thiazoline-related compound has an anti-inflammatory effect in sepsis model animals.

Example 21: Elongation Effect of Survival Time in Sepsis Animal Model by Intraperitoneal Administration of Thiazoline-Related Compound Experiment Method A sepsis model mouse was prepared by the same method as in Example 18. Immediately after the LPS administration, 200 μl (about 80 mg/kg) of a thiazoline-related compound (2MT) solution prepared by diluting 100 times with saline was intraperitoneally administered. The survival time of the mouse was measured when the thiazoline-related compound (2MT) was administered and when saline, as a control, was administered (saline).

Figure 21:
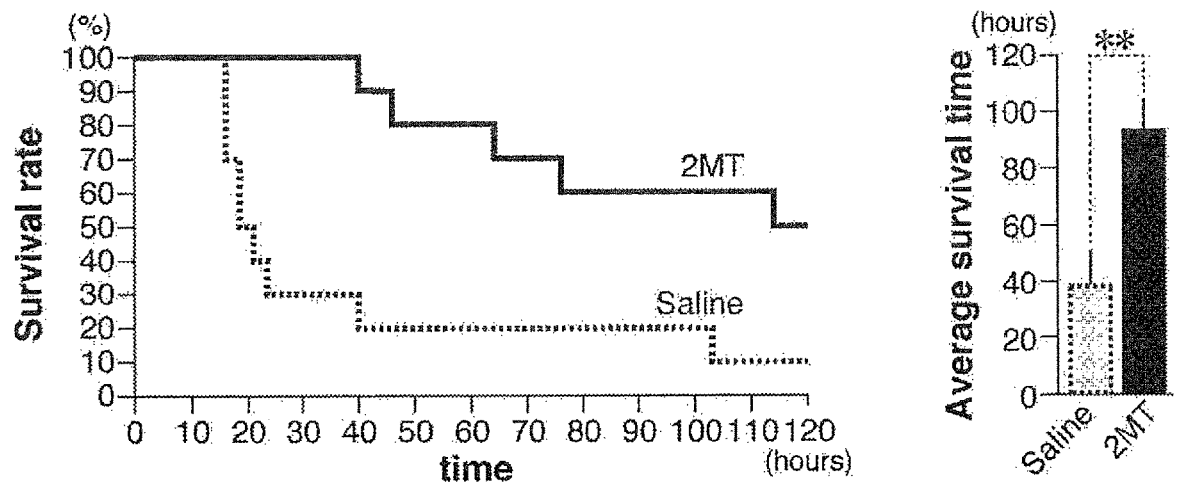
FIG. 21 shows the survival time by the Kaplan-Meier curve and bar graph (mean±standard error) when 2MT was intraperitoneally injected to a sepsis model mouse.

Results
The results are shown in FIG. 21.

Survival curves are shown for the control group (saline) and the group administered with the thiazoline-related compound (2MT) (left Figure). Also, the average survival time (mean±standard error) for each group is shown in a bar graph (n=10; right Figure). Student's t-test was performed between the control group and the group administered with thiazoline-related compound (2MT). ** means a significant difference at p<0.01. It was shown that administration of the thiazoline-related compound has an effect of extending the survival time in sepsis model animals.

Example 22: Mitigation Effect of Cerebral Ischemia-Reperfusion Injury by Thiazoline-Related Compound Experiment Method The bilateral common carotid arteries of about 3-month-old C57/BL6 mouse were ligated by clips to induce cerebral ischemia injury, and the blood was reperfused by removing the clips 30 min later. A thiazoline-related compound (2MT) solution (200 µl, about 80 mg/kg), or saline, as a control, was intraperitoneally administered at the reperfusion. Two days after the reperfusion, the brain tissue of the mouse was removed, brain sections were prepared, and the injured region was analyzed by antibody staining with Microtubule-associated protein 2 (MAP2).

Results

Figure 22:
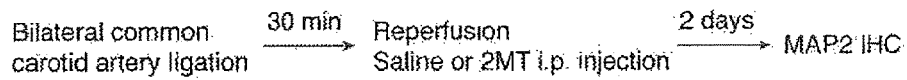
FIG. 22 shows tissue staining of the brain and quantification of the area of the injured region in a cerebral ischemia-reperfusion injury model mouse.
Figure 22:
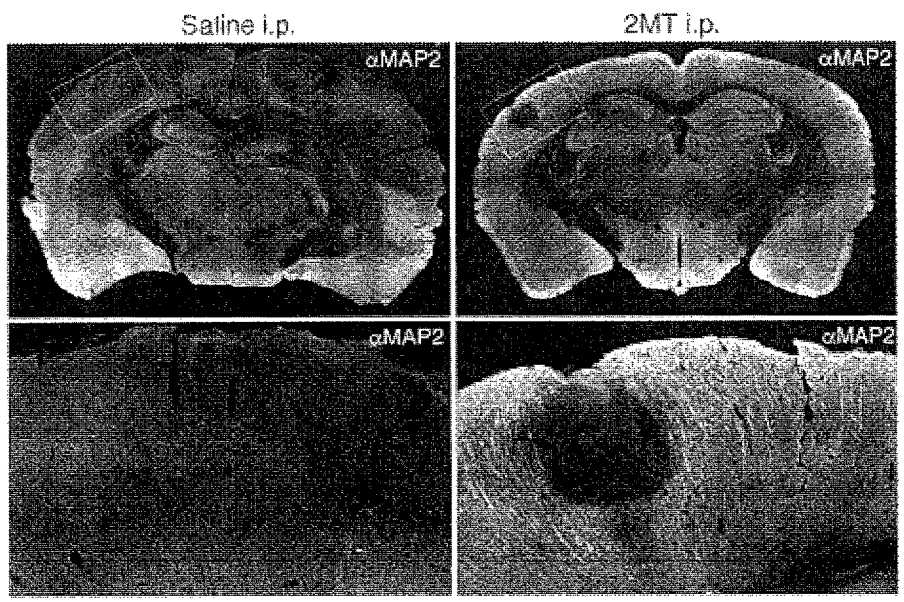
Figure 22:
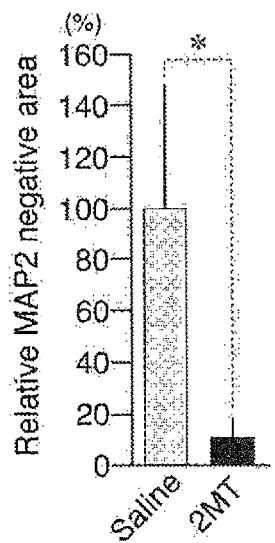

The results are shown in FIG. 22.

The protocol of the experiment is shown at the top of the Figure. Representative examples of the brain sections of the control and the animal administered with thiazoline-related compound, stained with MAP2 antibody, are shown on the left side of the Figure. In the Figure, the damaged region of the brain is observed as a region not stained with MAP2 (black). On the right side of the Figure, the area of the region not stained with MAP2 in the control group and the group administered with thiazoline-related compound (2MT), that is, the area of the injured region (mean±standard error), is shown in a bar graph (n=9 for saline, n=8 for 2MT). Student's t-test was performed between the control group and the group administered with thiazoline-related compound (2MT). * means a significant difference at p<0.05. It was shown that administration of the thiazoline-related compound at the reperfusion has an effect to reduce cerebral ischemia-reperfusion injury.

Example 23: Anti-Hypoxic Effect of Administration of Heterocyclic Compound Mediated by Trpa1

Experiment Method

Various heterocyclic compound solutions (200 µl, about 80 mg/kg) diluted 100 times with saline were intraperitoneally injected to male Trpa1 knockout and wild-type mice (about 3 to 6-month-old) and, 30 min later, the mice were placed in a tight box in which the oxygen concentration was adjusted to 4%, and the survival time of the mice was measured up to 30 min at maximum.

Results

Figure 23:
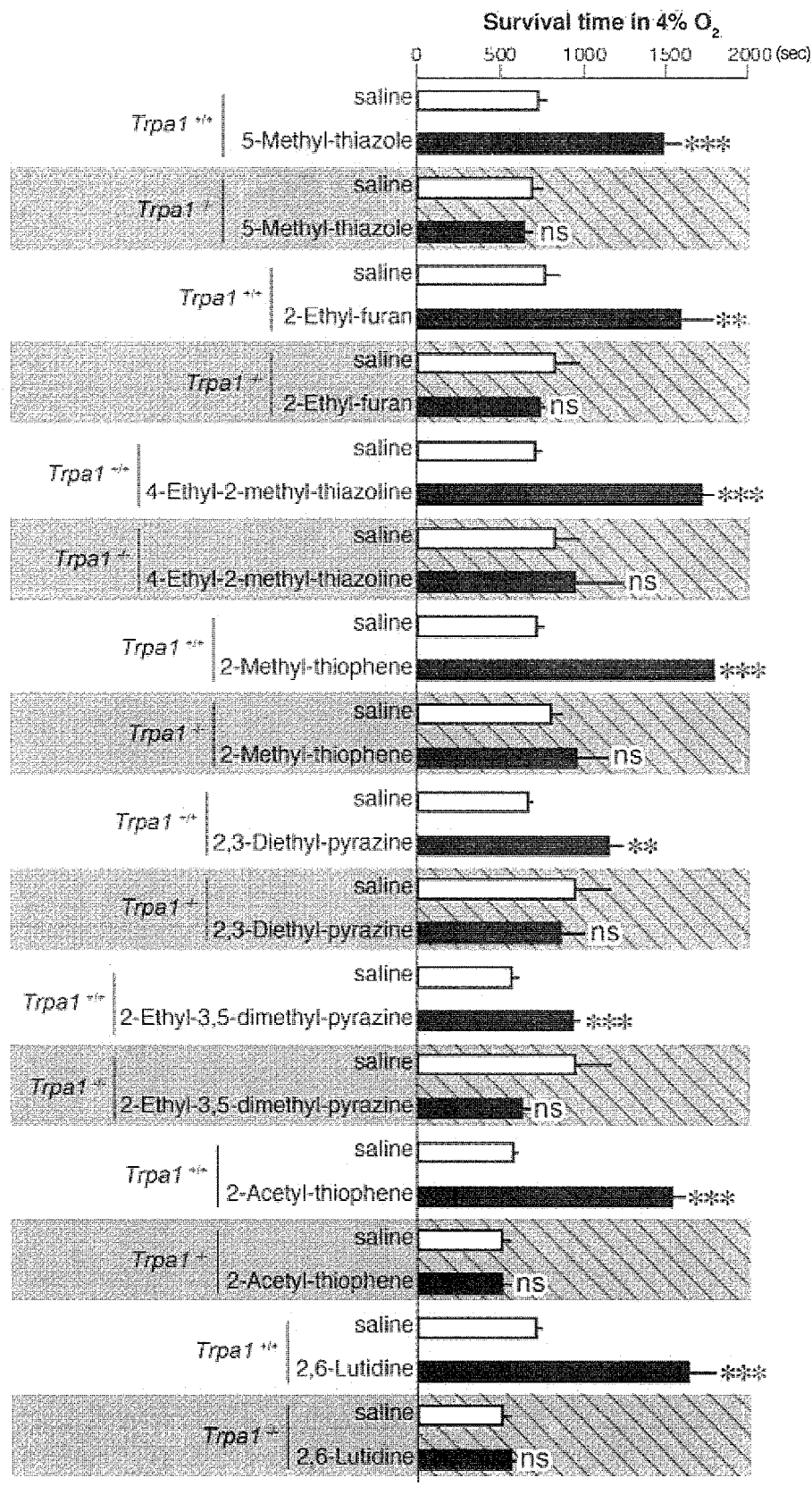
FIG. 23 shows the survival time (mean±standard error) in 4% oxygen when each heterocyclic compound was intraperitoneally administered to the control mouse (Trpa1$^{+/+}$) and Trpa1 knockout mouse (Trpa1$^{-/-}$).

The results are shown in FIG. 23. In FIG. 23, "4-Ethyl-2-methyl-thiazoline" means 4-ethyl-2-methyl-2-thiazoline. FIG. 23 is a bar graph showing the survival time (mean±standard error) in 4% oxygen when saline or heterocyclic compound was administered to wild-type mice (Trpa1$^{+/+}$) and Trpa1 knockout mice (Trpa1$^{-/-}$) (n=4). Student's t-test was performed for respective conditions between the control group (saline) and the group administered with each compound.  means a significant difference at p<0.01, * means a significant difference at p<0.001, and ns means no significant difference at p>0.05. Various kinds of heterocyclic compounds have an effect of significantly increasing the survival time under hypoxic conditions when administered to the wild-type mice; however, such effect was not observed in the Trpa1 knockout mice. Therefore, it was suggested that the hypoxia resistance by these heterocyclic compounds is mediated by Trpa1.

Example 24: Anti-Hypoxic Effect of Thiomorpholine Administration Mediated by Trpa1

Experiment Method

A heterocyclic compound (thiomorpholine) (200 µl, about 80 mg/kg) diluted 100 times with saline was intraperitoneally injected to male wild-type and Trpa1 knockout mice (about 3 to 6-month-old) and, 30 min later, the mice were placed in a tight box in which the oxygen concentration was adjusted to 4%, and the survival time of the mice was measured.

Results

Figure 24:
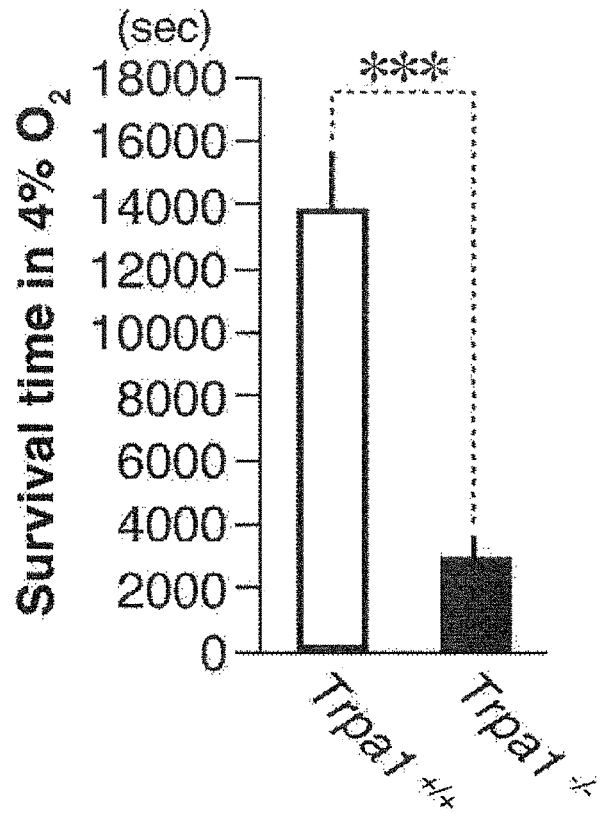
FIG. 24 shows the survival time (mean±standard error) in 4% oxygen when Thiomorpholine was intraperitoneally administered to the control mouse (Trpa1$^{+/+}$) and Trpa1 knockout mouse (Trpa1$^{-/-}$).

The results are shown in FIG. 24.

FIG. 24 is a bar graph showing the survival time (mean±standard error) in 4% oxygen when thiomorpholine was administered to wild-type mice (Trpa1$^{+/+}$) and Trpa1 knockout mice (Trpa1$^{-/-}$) (n=6). Student's t-test was performed between the control group (saline) and compound administration group. *** means a significant difference at p<0.001. The heterocyclic compound (thiomorpholine) has an effect of significantly prolonging the survival time under hypoxic conditions when administered to the wild-type mouse; however, the survival time significantly decreased in the Trpa1 knockout mouse as compared with the wild-type mouse. Therefore, it was shown that the hypoxia resistance by thiomorpholine is mediated by Trpa1.

Example 25: Suppression of Oxygen Consumption Induced by Administration of Thiazoline-Related Compound Mediated by Trpa1

Experiment Method

The oxygen consumption was measured using an energy metabolism measurement device for small animals as in Example 8. About 3-month to 6-month-old Trpa1 knockout mice and littermate hetero mice were each placed in a measuring chamber of the energy metabolism measurement device for small animals and, after acclimation for about 2 hr, a thiazoline-related compound (2MT) was presented. The odor was presented by placing two filter papers scented with 271 µmol of thiazoline-related compound (2MT) in the measuring chamber.

Results

Figure 25:
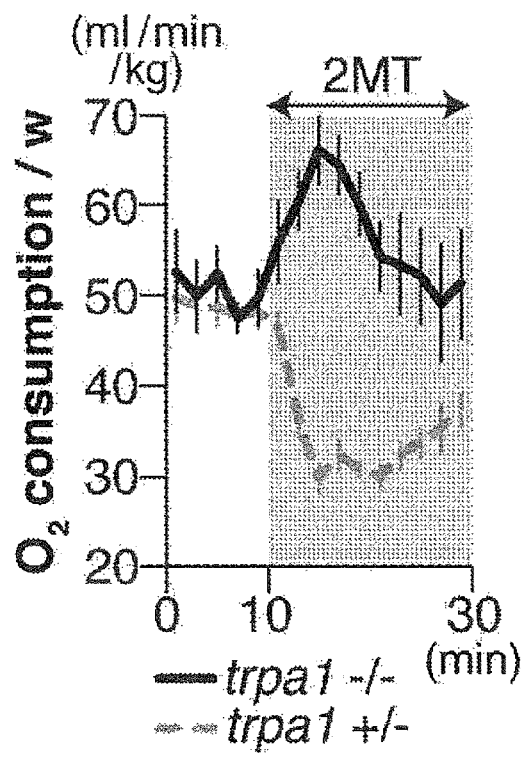
FIG. 25 shows time-course changes (mean±standard error) in the oxygen consumption when 2MT was presented to the control mouse (Trpa1$^{+/-}$) and Trpa1 knockout mouse (Trpa1$^{-/-}$).

The results are shown in FIG. 25.

FIG. 25 shows time-course changes (mean±standard error) in the oxygen consumption per body weight of control mice (Trpa1$^{+/-}$; n=9) and Trpa1 knockout mice (Trpa1$^{-/-}$; n=7) when the thiazoline-related compound (2MT) was presented. The odor was presented at the time point of 10 min in the Figure. In the control mice, the oxygen consumption was decreased when the thiazoline-related compound (2MT) was presented; however, the oxygen consumption did not decrease in the Trpa1 knockout mice. Therefore, it was shown that the thiazoline-related compound decreases oxygen consumption via Trpa1.

Example 26: Anti-Hypoxic Effects Induced by Administration of Trpa1 Agonist

Experiment Method

Saline or known Trpa1 agonists Δ9-tetrahydrocannabinol ($\Delta^9$-THC; 10 mg/kg), allyl isothiocyanate (AITC; 40 mg/kg), or acetaminophen (APAP; 300 mg/kg) was intraperitoneally administered to male C57/BL6N mouse (about 3-month-old) and, 30 min later, the mouse was placed in a tight box with adjusted oxygen concentration of 4%, and the survival time of the mouse was measured for 30 min at maximum. As to APAP, the survival time in 4% oxygen environment was also measured using male Trpa1 knockout and littermate hetero mice (about 3- to 6-month-old).

Results

Figure 26:
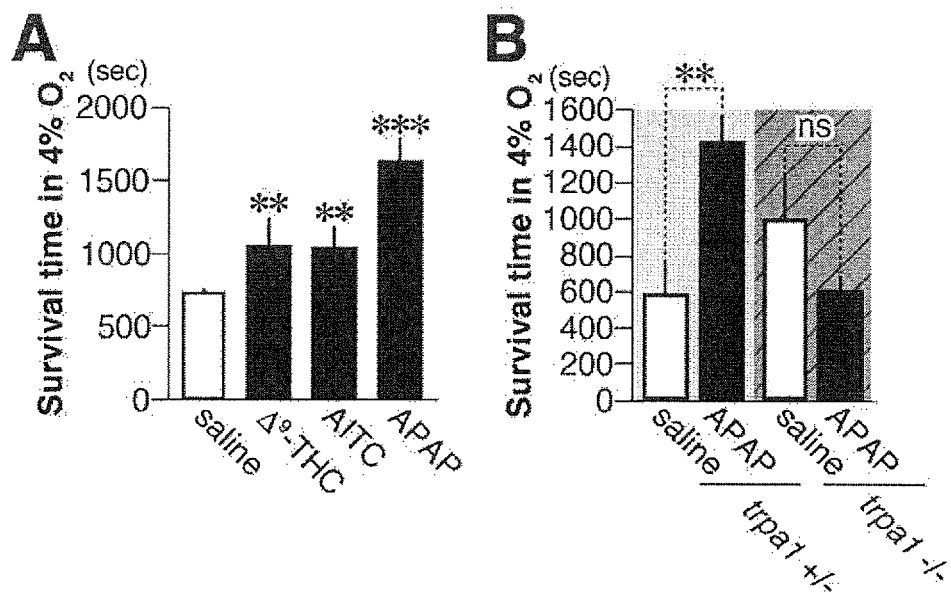
FIG. 26 A: Figure showing the survival time (mean±standard error) in 4% oxygen when each Trpa1 agonist was administered. B: Figure showing the survival time (mean±standard error) in 4% oxygen when acetaminophen was administered to the control mouse (Trpa1$^{+/+}$, Trpa1$^{+/-}$) and Trpa1 knockout mouse (Trpa1$^{-/-}$).

The results are shown in FIG. 26.

FIG. 26A is a bar graph showing the survival time (mean±standard error) in 4% oxygen when saline or various Trpa1 agonists were administered to wild-type mouse (n=22 for saline, n=8 for $\Delta^9$-THC, AITC, n=7 for APAP). Student's t-test was performed between the control group and the group administered with Trpa1 agonist.  means a significant difference at $p<0.01$, and * means a significant difference at $p<0.001$. The administration of Trpa1 agonist showed an effect of extending the survival time under a hypoxic environment.

FIG. 26B is a bar graph showing the survival time (mean±standard error) of the control mice (Trpa1$^{+/-}$) and Trpa1 knockout mice (Trpa1$^{-/-}$) in 4% oxygen when Trpa1 agonist (APAP) was intraperitoneally administered (n=8). Student's t-test was performed between the control group (saline) and the group administered with Trpa1 agonist (APAP). ** means a significant difference at $p<0.01$, and ns means no significant difference at $p>0.05$. The Trpa1 agonist (APAP) has an effect of extending the survival time under a hypoxic environment in the control mice, whereas such effect was not observed in the Trpa1 knockout mice. It was shown that the Trpa1 agonist induces hypoxia resistance via Trpa1.

Example 27: Effect of Body Surface Temperature Change, Hypoxia Resistance and Anti-Inflammatory Action Induced by Thiazoline-Related Compound in Trpa1 Knockout Mouse Experiment Method Changes in the body surface temperature, survival time under a hypoxic environment, and TNF-α production in blood by LPS administration induced by intraperitoneally administration of thiazoline-related compound (4-ethyl-2-methyl-2-thiazoline; 4E2MT) measured by a method similar to those in Example 3, Example 10, or Example 18.

Results

Figure 27:
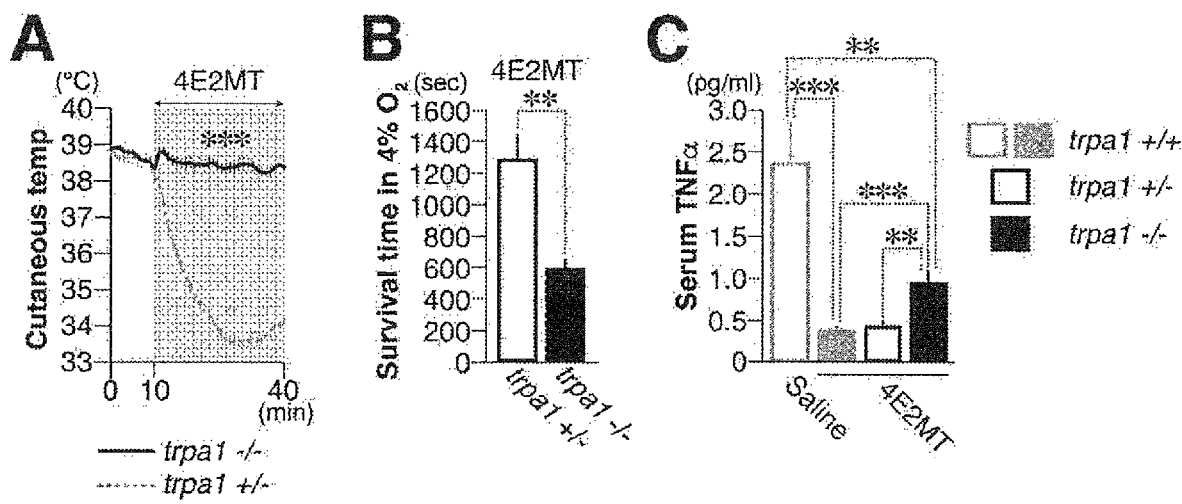
FIG. 27 A: Figure showing time-course changes (mean±standard error) in the body surface temperature when 4E2MT (4-Ethyl-2-methyl-2-thiazoline) was intraperitoneally injected to the control mouse (Trpa1$^{+/-}$) and Trpa1 knockout mouse (Trpa1$^{-/-}$). B: Figure showing the survival time (mean±standard error) in 4% oxygen when 4E2MT was intraperitoneally injected to the control mouse (Trpa1$^{+/-}$) and Trpa1 knockout mouse (Trpa1$^{-/-}$). C: Figure showing the amount of TNF-α in blood (mean±standard error) when LPS (Lipopolysaccharide) and 4E2MT were administered to the control mouse (Trpa1$^{+/+}$, Trpa1$^{+/-}$) and Trpa1 knockout mouse (Trpa1$^{-/-}$).

The results are shown in FIG. 27.

FIG. 27A shows time-course changes (mean±standard error) in the body surface temperature when thiazoline-related compound (4E2MT) was intraperitoneally injected to the control mice (Trpa1$^{+/-}$) and Trpa1 knockout mice (Trpa1$^{-/-}$). The thiazoline-related compound (4E2MT) was administered at 10 min time point. Student's t-test was performed for the mean surface temperature 30 min after administration of thiazoline-related compound (4E2MT) between the control and Trpa1 knockout mice. The results are shown in the Figure. *** means a significant difference at $p<0.001$. It was clarified that a decrease in the body surface temperature induced by intraperitoneal administration of the thiazoline-related compound was not observed in Trpa1 knockout mice.

FIG. 27B is a bar graph showing the survival time (mean±standard error) in 4% oxygen when thiazoline-related compound (4E2MT) was intraperitoneally injected to the control mice (Trpa1$^{+/-}$) and Trpa1 knockout mice (Trpa1$^{-/-}$). Student's t-test was performed between the control group and the Trpa1 knockout group. ** means a significant difference at $p<0.01$. It was clarified that the elongation effect of survival time under a hypoxic environment induced by intraperitoneal administration of thiazoline-related compound was suppressed in Trpa1 knockout mice.

FIG. 27C is a bar graph showing the amount of TNF-α in blood (mean±standard error) 1 hr after simultaneous intraperitoneal administration of thiazoline-related compound (4E2MT) and LPS. As a control, blood TNF-α amount was also measured when LPS and saline were administered to the control mice (Trpa1$^{+/+}$).  means a significant difference at $p<0.01$, and * means a significant difference at $p<0.001$. The amount of inflammatory cytokine TNF-α in blood was decreased by administration of the thiazoline-related compound (4E2MT) in the sepsis mouse model. It was shown that this effect was suppressed in Trpa1 knockout mice.

From the results of FIG. 27A-C, it was shown that the body surface temperature decrease, hypoxia resistance, and anti-inflammatory effect induced by the thiazoline-related compound are mediated by Trpa1.

Example 28: Suppression of Oxygen Consumption Induced by Heterocyclic Compound Experiment Method Changes in the oxygen consumption induced by intraperitoneal injection of heterocyclic compounds (2MT and Thiomorpholine (TMO)) were measured by a method similar to that in Example 8.

Results

Figure 28:
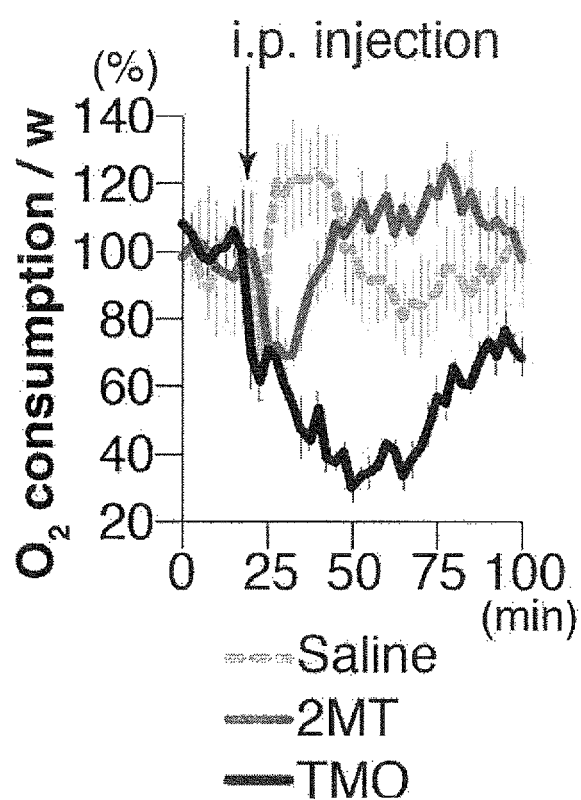
FIG. 28 shows time-course changes (mean±standard error) in the oxygen consumption when thiomorpholine (TMO) and 2MT were intraperitoneally administered.

The results are shown in FIG. 28.

FIG. 28 shows time-course changes (mean±standard error) in the oxygen consumption when heterocyclic compounds (2MT, TMO) and saline were administered (n=4). The heterocyclic compounds (2MT, TMO) and saline were administered at the time points shown with arrows in the Figure. It was shown that the administration of the heterocyclic compounds has an effect to suppress the oxygen consumption.

INDUSTRIAL APPLICABILITY

Since the compound of the present invention shows induction of hypothermia, hypometabolism, suppression of oxygen consumption, low heart rate, anti-inflammatory reaction, protection action on tissues and individuals under hypoxic conditions, protection action against ischemia-reperfusion injury, and protection action against inflammation, it is useful as a prophylactic or therapeutic agent for hypoxic injury, ischemia-reperfusion injury or inflammation, an agent for protecting cells for transplantation, or an agent for preserving organism.

The invention claimed is:

1. A method for treating ischemia-reperfusion injury in a mammal, comprising administering to the mammal an effective amount of a compound represented by the formula

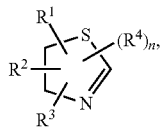

or a salt thereof,
wherein $R^1$, $R^2$, $R^3$ and $R^4$ are each independently a hydrogen atom, a $C_{1-6}$ alkyl group, a $C_{1-6}$ alkylthio group, or a $C_{2-6}$ alkenylthio group; and n is 0, 1, or 2.

2. The method according to claim 1, wherein the compound is selected from the group consisting of 2-methyl-2-thiazoline, 2-(methylthio)-2-thiazoline, 2-sec-butyl-2-thiazoline, 4-ethyl-2-methyl-2-thiazoline, and 2-(allylthio)-2-thiazoline.

3. The method according to claim 1, wherein the compound is intranasally administered.

4. The method according to claim 1, wherein the compound is 2-(methylthio)-2-thiazoline.

5. The method according to claim 1, wherein the compound is 2-sec-butyl-2-thiazoline.

6. The method according to claim 1, wherein the compound is 4-ethyl-2-methyl-2-thiazoline.

7. The method according to claim 1, wherein the compound is 2-(allylthio)-2-thiazoline.

8. A method for treating ischemia-reperfusion injury in a mammal, comprising administering an effective amount of 2-methyl-2-thiazoline or a salt thereof to the mammal.

9. The method according to claim 8, wherein 2-methyl-2-thiazoline or a salt thereof is intranasally administered.

* * * * *